(12) United States Patent
Ertl et al.

(10) Patent No.: US 9,744,224 B2
(45) Date of Patent: Aug. 29, 2017

(54) METHODS FOR TREATING CANCER BY ADMINISTRATION OF NUCLEIC ACIDS ENCODING FAP AND CANCER ANTIGENS

(71) Applicant: The Wistar Institute of Anatomy and Biology, Philadelphia, PA (US)

(72) Inventors: Hildegund C. J. Ertl, Villanova, PA (US); Ying Zhang, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/190,794

(22) Filed: Jun. 23, 2016

(65) Prior Publication Data
US 2016/0296612 A1   Oct. 13, 2016

Related U.S. Application Data

(62) Division of application No. 14/212,099, filed on Mar. 14, 2014, now Pat. No. 9,402,888.

(60) Provisional application No. 61/781,429, filed on Mar. 14, 2013.

(51) Int. Cl.
| | | |
|---|---|---|
| *A61K 39/12* | (2006.01) | |
| *A61K 39/00* | (2006.01) | |
| *A61K 38/48* | (2006.01) | |
| *A61K 48/00* | (2006.01) | |

(52) U.S. Cl.
CPC .......... *A61K 39/0011* (2013.01); *A61K 38/48* (2013.01); *A61K 38/482* (2013.01); *A61K 48/0058* (2013.01); *C12Y 304/14005* (2013.01); *A61K 2039/522* (2013.01); *A61K 2039/53* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 5,240,846 A | 8/1993 | Collins | |
| 6,083,716 A | 7/2000 | Wilson | |
| 7,247,472 B2 | 7/2007 | Wilson | |
| 8,962,816 B2* | 2/2015 | Ertl | A61K 39/245 536/23.1 |
| 9,044,420 B2* | 6/2015 | Dubensky, Jr. | A61K 39/0011 |

FOREIGN PATENT DOCUMENTS

| | | |
|---|---|---|
| WO | WO 00/11140 | 3/2000 |
| WO | WO 2005/071093 | 8/2005 |

OTHER PUBLICATIONS

Lee et al (Cancer Research, 2005, 65:11156-11163, IDS).*
Lasaro et al (Microbes and Infection, 2005, 7:1541-1550, IDS).*
Ahmadzadeh M, et al., Tumor antigen-specific CD8 T cells infiltrating the tumor express high levels of PD-1 and are functionally impaired. Blood, Aug. 2009; 114(8): 1537-1544.
Alexandrescu DT et al., Immunotherapy for melanoma: current status and perspectives. J Immunotherapy, Jul. 2010; 33:570-590.
Algazi AP et al., Treatment of cutaneous melanoma: current approaches and future prospects. Cancer Manag Res, Aug. 2010; 2: 197-211.
Ariga N, et al. Stromal expression of fibroblast activation protein/seprase, a cell membrane serine proteinase and gelatinase, is associated with longer survival in patients with invasive ductal carcinoma of breast. Int. J. Cancer, Jan. 2001; 95: 67-72.
Bai A, et al., Rapid tolerization of virus-activated tumor-specific CD8+ T cells in prostate tumors of TRMAP mice. Proc Natl Acad Sci, USA, Sep. 2008; 105:13003-13008.
Bhowmick NA, et al. Stromal fibroblasts in cancer initiation and progression. Nature, Nov. 2004; 432: 332-337.
Bloom, MB et al., Identification of tyrosinase-related protein 2 as tumor rejection antigen for the B16 melanoma. J. Exp. Med., Feb. 1997; 185(3): 453-459.
Bronte V. et al. Genetic Vaccination with "Self" Tyrosinase-related Protein 2 causes melanoma eradication but not Vitiligo. Cancer Res, Jan. 2000; 60(2): 253-258.
Cheng JD, et al. Promotion of tumor growth by murine fibroblast activation protein, a serine protease, in an animal model. Cancer Res, Aug. 2002; 62: 4767-4772.
Dankort D, et al. BrafV600E cooperates with Pten loss to induce metastatic melanoma. Nature Genetics, May 2009; 41(5): 544-552.
Dankort D, et al. A new mouse model to explore the initiation, progression, and therapy of Brafv600E-induced lung tumors. Genes Dev., Feb. 2007; 21: 379-384.
Su Z, et al. Enhanced induction of telomerase-specific CD4+ T cell using dendritic cells transfected with RNA encoding a chimeric gene product. Cancer Res. Sep. 2002; 62: 5041-5048.
Derré L, et al., BTLA mediates inhibition of human tumor-specific CD8+T cells that can be partially reversed by vaccination. J.Clin. Invest., Jan. 2010; 120: 157-167.
Dimenna L, et al. Augmentation of primary influenza A virus-specific CD8+T cell responses in aged mice through blockade of an immunoinhibitory pathway. J Immunol., Apr. 2010; 184(10): 5475-84.

(Continued)

Primary Examiner — Laura B Goddard
(74) Attorney, Agent, or Firm — Howson & Howson LLP

(57) ABSTRACT

A immunogenic composition is provided for use in methods for treating or preventing the development of a cancer, comprising a nucleic acid sequence encoding a cancer antigen and a nucleic acid sequence encoding fibroblast activation protein (FAP). In one embodiment, the composition comprises a vector comprising a first expression cassette comprising a nucleic acid sequence encoding an antigen of a, operatively linked to an expression control sequence that directs the expression of the antigen in a mammalian host cell. The composition further contains a vector comprising a second expression cassette comprising a nucleic acid sequence encoding fibroblast activation protein (FAP) operatively linked to an expression control sequence directing the expression of FAP in a mammalian host cell. In one embodiment, the cancer is one in which tumor progression depends on the fibroblasts expressing fibroblast activation protein (FAP).

12 Claims, 21 Drawing Sheets

(56) References Cited

OTHER PUBLICATIONS

Fassnacht M, et al. Induction of CD4+ and CD8+ T-Cell responses to the human stromal antigen, fibroblast activation protein: implication for cancer immunotherapy. Clin Cancer Res., Aug. 2005; 11(15): 5566-5571.

Fourcade J, et al. Upregulation of Tim-3 and PD-1 expression is associated with tumor antigen-specific CD8+T cell dysfunction in melanoma patients. Journal of Experimental Medicine, Sep. 2010; 207(10): 2175-2186.

Gajewski TF. Failure at the effector phase: immune barriers at the level of the melanoma tumor microenvironment. Clin Cancer Res., Sep. 2007; 13: 5256-5261.

Lee J, et al. Tumor immunotherapy targeting fibroblast activation protein, a product expressed in tumor-associated fibroblast. Cancer Res., Dec. 2005; 65: 11156-11163.

Guevara-Patino J, et al. Optimization of a self antigen for presentation of multiple epitopes in cancer immunity. J. Clin. Invest., May 2006; 116(5): 1382-1390.

Hodi FS, et al. Improved Survival with Ipilimumab in Patients with Metastatic Melanoma. N Engl J Med., Aug. 2010; 363:711-723.

Huber MA., et al. Fibroblast activation protein: Differential expression and serine protease activity in reactive stromal fibroblasts of melanocytic skin tumors. Journal of investigative Dermatology, Feb. 2003; 120(2): 182-188.

Janicki CN, et al. Loss of function among high-avidity tumor-specific CD8+ T cells following tumor infiltration. Cancer Res., Apr. 2008; 68: 2993-3000.

Kaplan JM, et al. Induction of antitumor immunity with dendritic cells transduced with adenovirus vector-encoding endogenous tumor-associated antigen. J Immunol., Jul. 1999; 163: 699-707.

Kirkwood JM, et al. Strategies for the Development of More Effective Adjuvant Therapy of Melanoma: Current and Future Explorations of Antibodies, Cytokines, Vaccines, and Combinations. Clin Cancer Res., Apr. 2006; 12:2331s-2336s.

Klebanoff CA. et al., Therapeutic cancer vaccines: are we there yet?. Immunological Reviews, Jan. 2011; 239: 27-44.

Lasaro MO, et al. Targeting of antigen to the herpesvirus entry mediator augments primary adaptive immune responses. Nature Medicine, Feb. 2008; 14(2): 205-212.

Liu Y, et al. Lentivector immunization stimulates potent CD8 T cell responses against melanoma self-antigen tyrosinase-related protein 1 and generates antitumor immunity in mice. J Immunol., May 2009; 182: 5960-5969.

Loeffler M, et al. Targeting tumor-associated fibroblasts improves cancer chemotherapy by increasing intratumoral drug uptake. J. Clin. Invest., Jul. 2006; 116(7): 1955-1962.

Michaloglou C, et al. Brafv600E-associated senescence-like cell cycle arrest of human naevi. Nature, Aug. 2005; 436: 720-726.

Naftzger C, et al. Immune response to a differentiation antigen induced by altered antigen: a study of tumor rejection and autoimmunity. Proc. Natl. Acad.Sci. USA, Dec. 1996; 93: 14809-14814.

Overwijk WW, et al. Vaccination with a recombinant vaccinia virus encoding a "self" antigen induces autoimmune vitiligo and tumor cell destruction in mice: Requirement for CD4+ T lymphocytes. Proc. Natl. Acad. Sci. USA, Mar. 1999; 96: 2982-2987.

Overwijk WW, et al. Tumor regression and autoimmunity after reversal of a functionally tolerant state of self-reactive CD8+ T Cells. Journal of Experimental Medicine, Aug. 2003; 198(4): 569-580.

Santos, AM et al. Targeting fibroblast activation protein inhibits tumor stromagenesis and growth in mice. J. Clin. Invest., Dec. 2009; 119: 3613-3625.

Rosenberg S, et al., Cancer immunotherapy: moving beyond current vaccines. Nat Medic., Sep. 2004; 10(9): 909-915.

Rosenberg S. Overcoming obstacles to the effective immunotherapy of human cancer. Proc. Natl. Acad.Sci. USA, Sep. 2008; 105(35): 12643-12644.

Schreurs MWJ, et al. Dendritic cells break tolerance and induce protective immunity against a melanocyte differentiation antigen in an autologous melanoma model. Cancer Research, Dec. 2000; 60: 6995-7001.

Singh V., et al., Melanoma progression despite infiltration by in vivo-Primed TRP-2-specific T cells. J. Immunother., Feb. 2009; 32(2):129-139.

Tatsis N, et al. Chimpanzee-origin adenovirus vectors as vaccine carriers. Gene Therapy, Mar. 2006; 13: 421-429.

Tatsis N, et al., Adenoviruses as vaccine vectors. Molecular Therapy, Oct. 2004;10(4): 616-629.

Tsukamoto K, et al. A second tyrosinase-related protein, TRP-2, is a melanogenic enzyme termed DOPAchrome tautomerase. EMBO J., Feb. 1992; 11(2): 519-526.

Uong A, et al., Melanocytes in development and cancer. J Cell Physiol., Jan. 2010; 222(1): 38-41.

Visonneau S, et al. Growth characteristics and metastatic properties of human breast cancer xenografts in immunodeficient mice. American Journal of Pathology, May 1998; 152(5): 1299-1311.

Weber LW, et al. Tumor immunity and autoimmunity induced by immunization with homologous DNA. J. Clin. Invest., Sep. 1998; 102(6): 1258-1264.

Wellbrock C, et al. V599EB-RAF is an oncogene in melanocytes. Cancer Res., Apr. 2004; 64: 2338-2342.

Wen Y, et al. Immunotherapy targeting fibroblast activation protein inhibits tumor growth and increases survival in a murine colon cancer model. Cancer Sci., Nov. 2010; 101(11): 2325-2332.

Cai G., GF Freemean, The CD160, BTLA, LIGHT/HVEM pathway: a bidirectional switch regulating T-cell activation. Immunological Reviews, May 2009; 229: 244-28.

Chin, L. The genetics of malignant melanoma: lessons from mouse and man. Nat. Rev. Cancer, Aug. 2003; 3: 559-570.

Davies, H. et al. Mutations of the Braf gene in human cancer. Nature, Jun. 2002; 417: 949-954.

De Stefano I, et al. Antiproliferative and antiangiogenic effects of the benzophenanthridine alkaloid sanguinarine in melanoma. Biochemical Pharmacology, Dec. 2009; 78(11): 1374-1381.

Dolcetti, L. et al., Hierarchy of immunosuppressive strength among myeloid-derived suppressor cell subsets is determined by GM-CSF. , Eur. J. Immunol., Jan. 2010, 40:22-35.

Gray-Schopfer V, et al. Melanoma biology and new targeted therapy. Nature, Feb. 2007; 445: 851-857.

Kraman M, et al., Suppression of Antitumor Immunity by Stromal Cells Expressing Fibroblast Activation Protein-α. Science, Nov. 2010; 330(5):827-830.

Millington, GWR, Mutations of the BRAF gene in human cancer, by Davies et al. (Nature 2002; 417: 949-54), Clin. Exp. Dermatol., Mar. 2013, 38:222-223.

Murphy KM, et al. Balancing co-stimulation and inhibition with BTLA and HVEM, Nat. Rev. Immunol., Sep. 2006; 6:671-681.

Priceman, SJ et al, Targeting distinct tumor-infiltrating myeloid cells by inhibiting CSF-1 receptor: combating tumor evasion of antiangiogenic therapy., Blood, Feb. 2010, 115(7):1461-1471.

Schreiber H, Rowley DA., Awakening Immunity. Science, Nov. 2010; 330: 761-762.

Šedý JR, et al., B and T lymphocyte attenuator regulates T cell activation through interaction with herpesvirus entry mediator. Nature Immunology, Jan. 2005; 6:90-98.

Sivendran S, et al. Melanoma Immunotherapy. Mt Sinai J Med., Nov. 2010; 77:620-642.

Trinh VA. Current management of metastatic melanoma. Am J Health Syst Pharm Dec. 2008; 65:S3-S8.

Turnis, M.E. and Rooney, C.M., Enhancement of Dendritic Cells as Vaccines for Cancer, Immunotherapy, Nov. 2010, 2(6): 847-862.

* cited by examiner

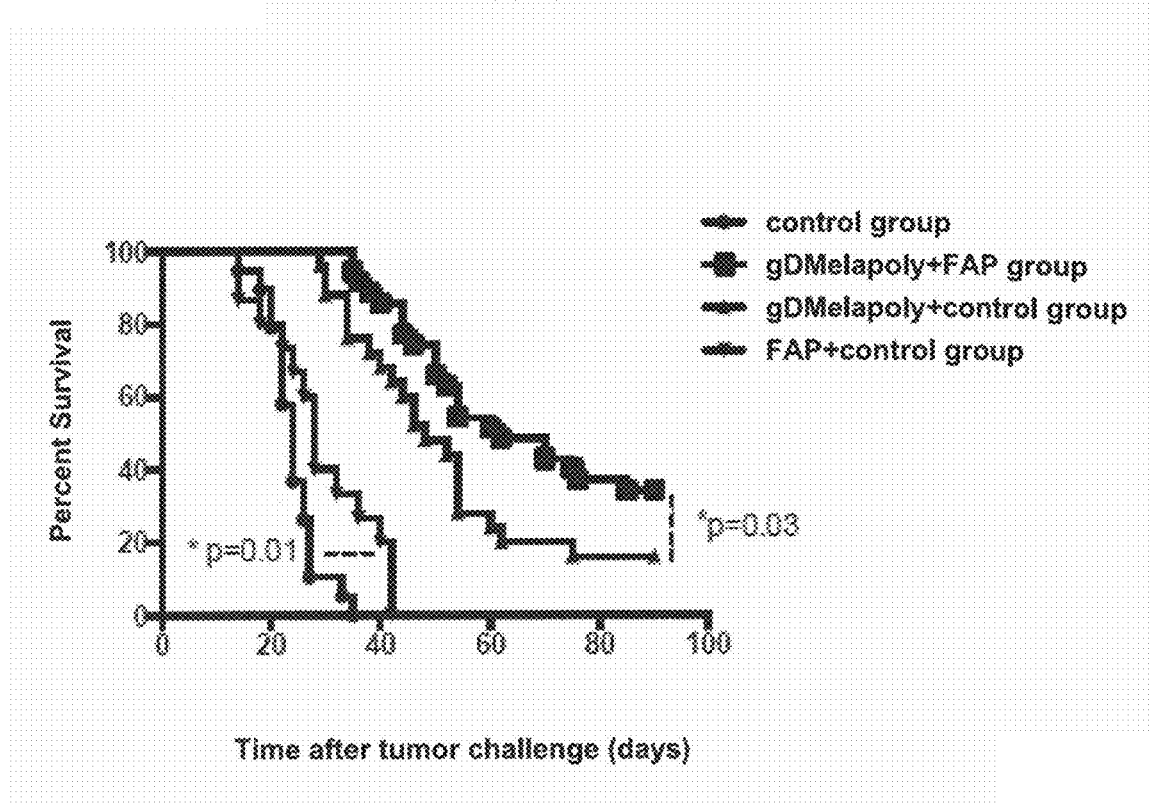

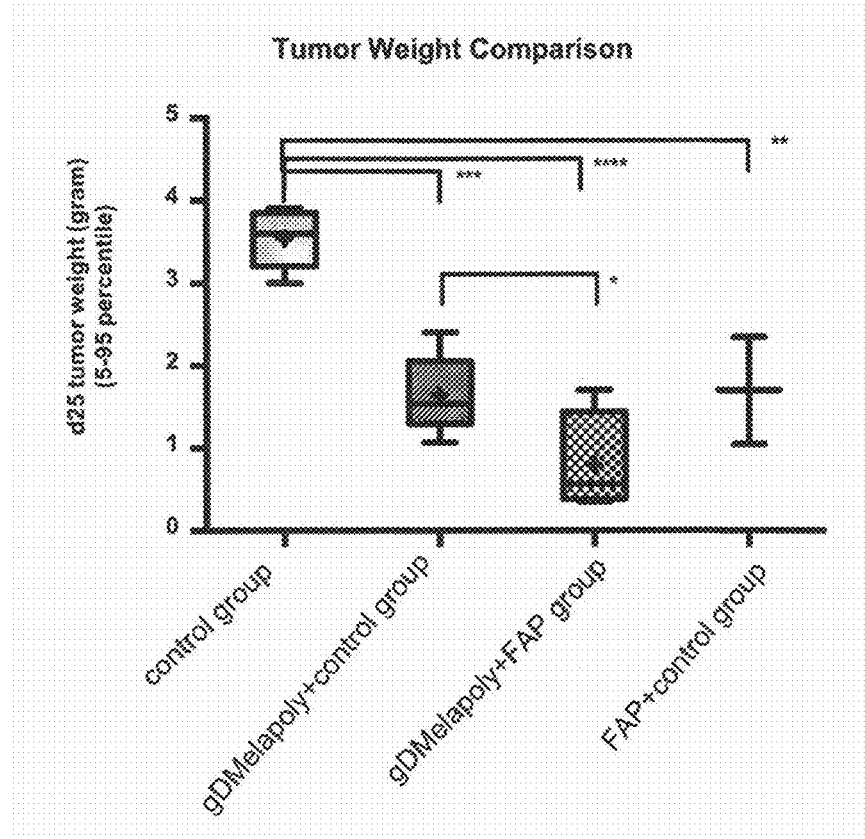

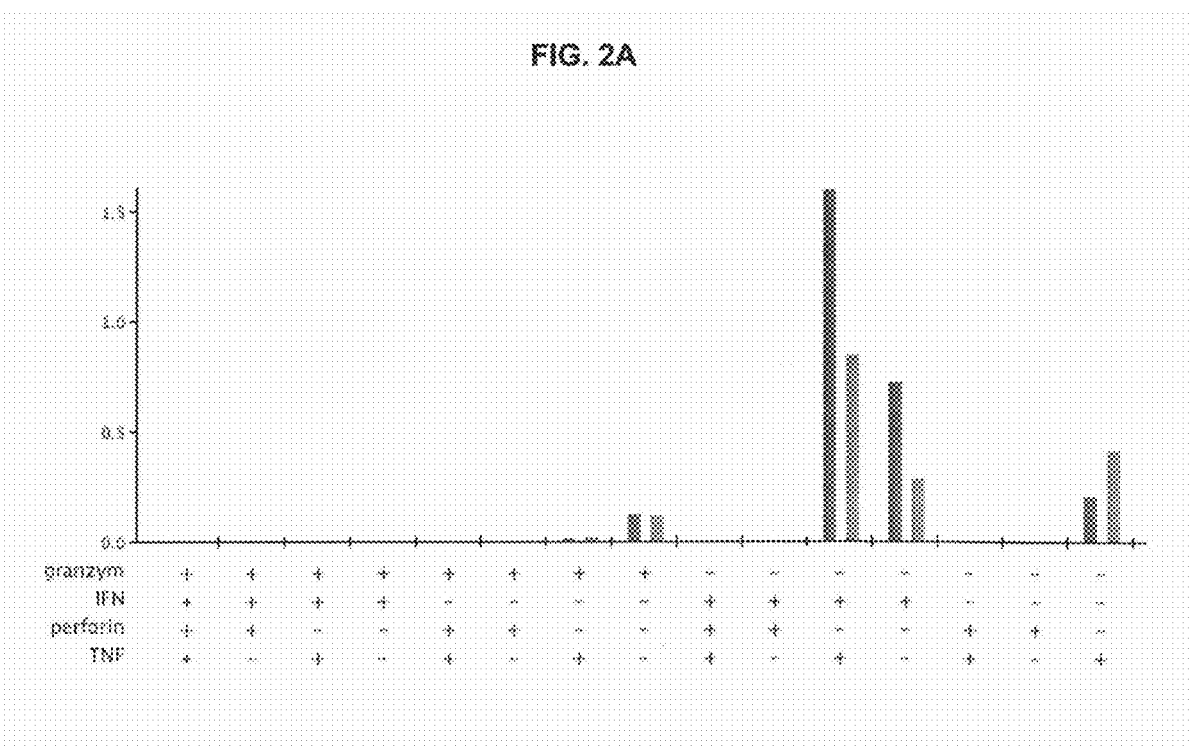

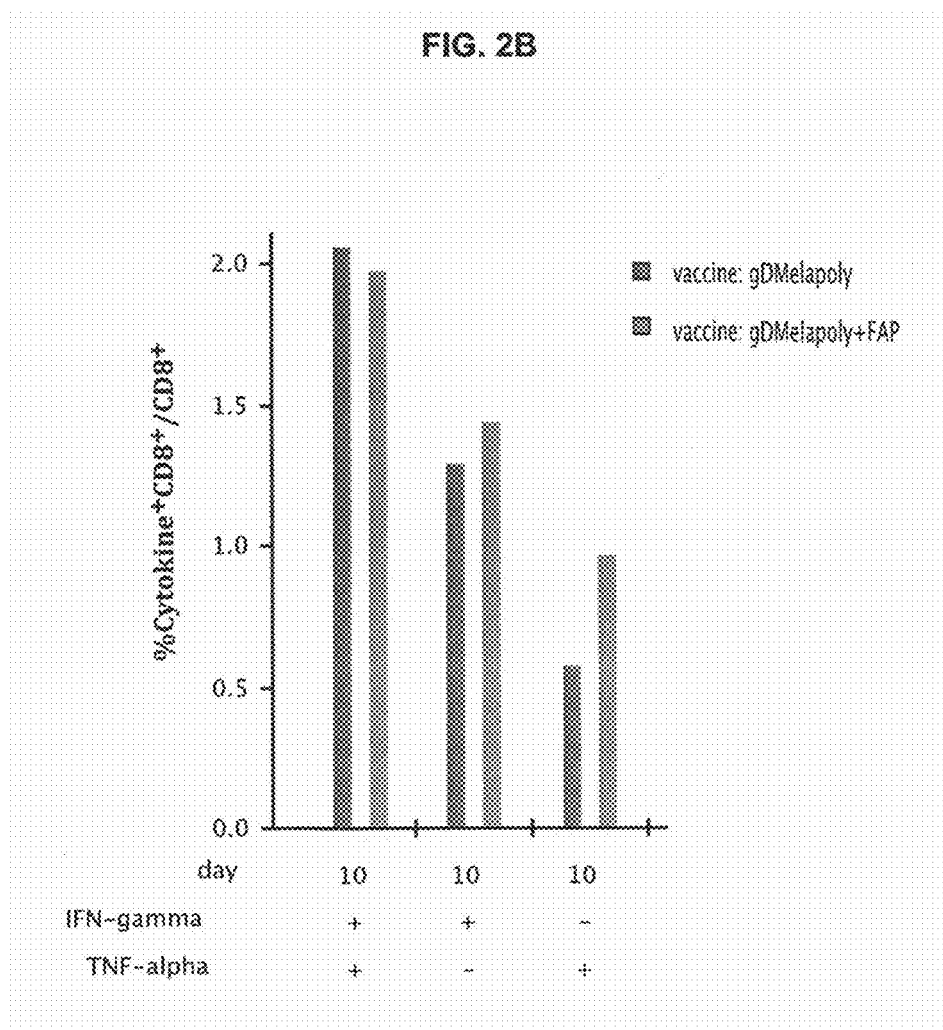

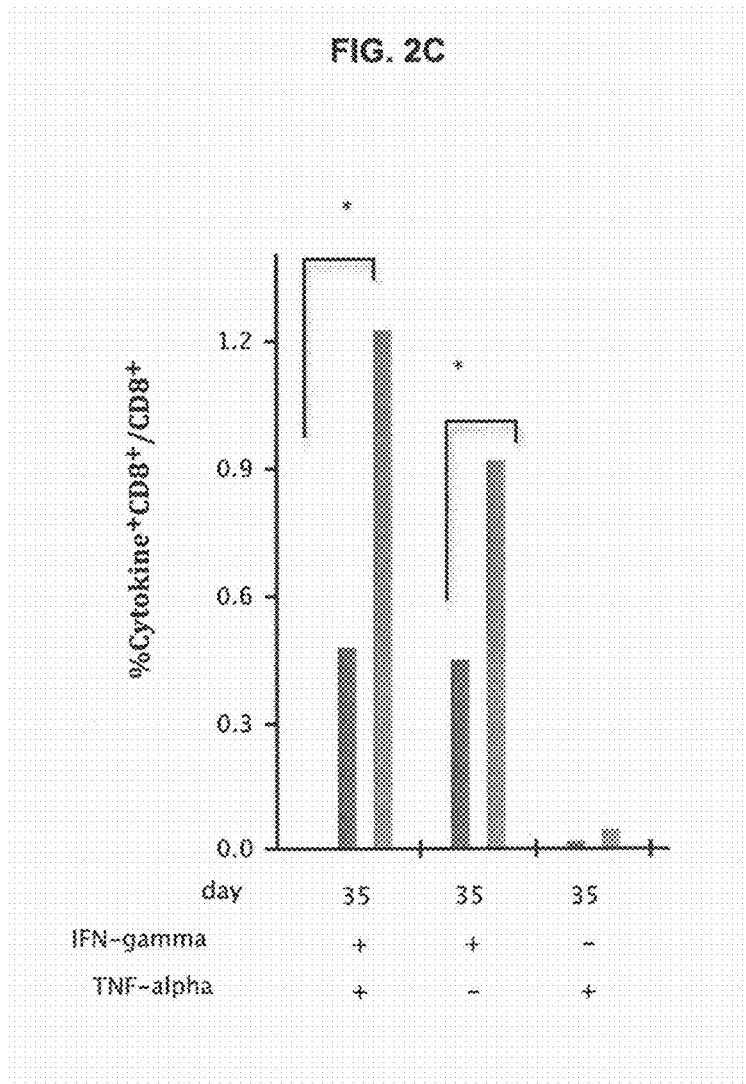

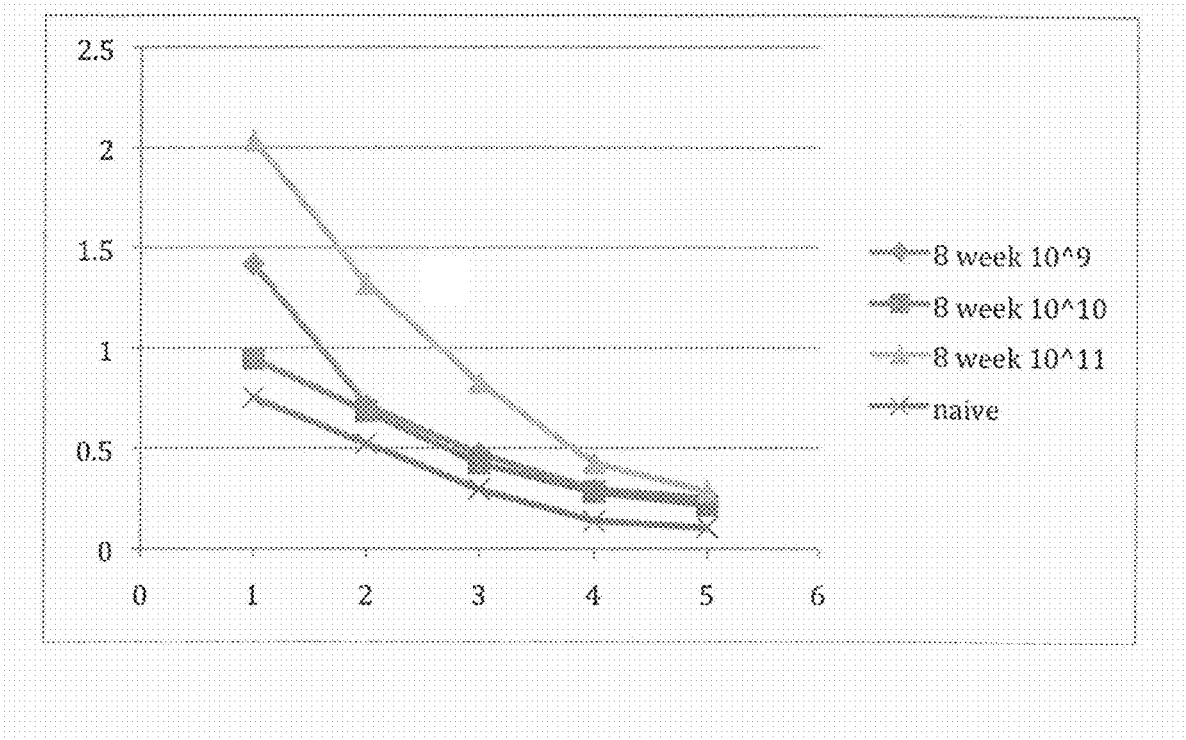

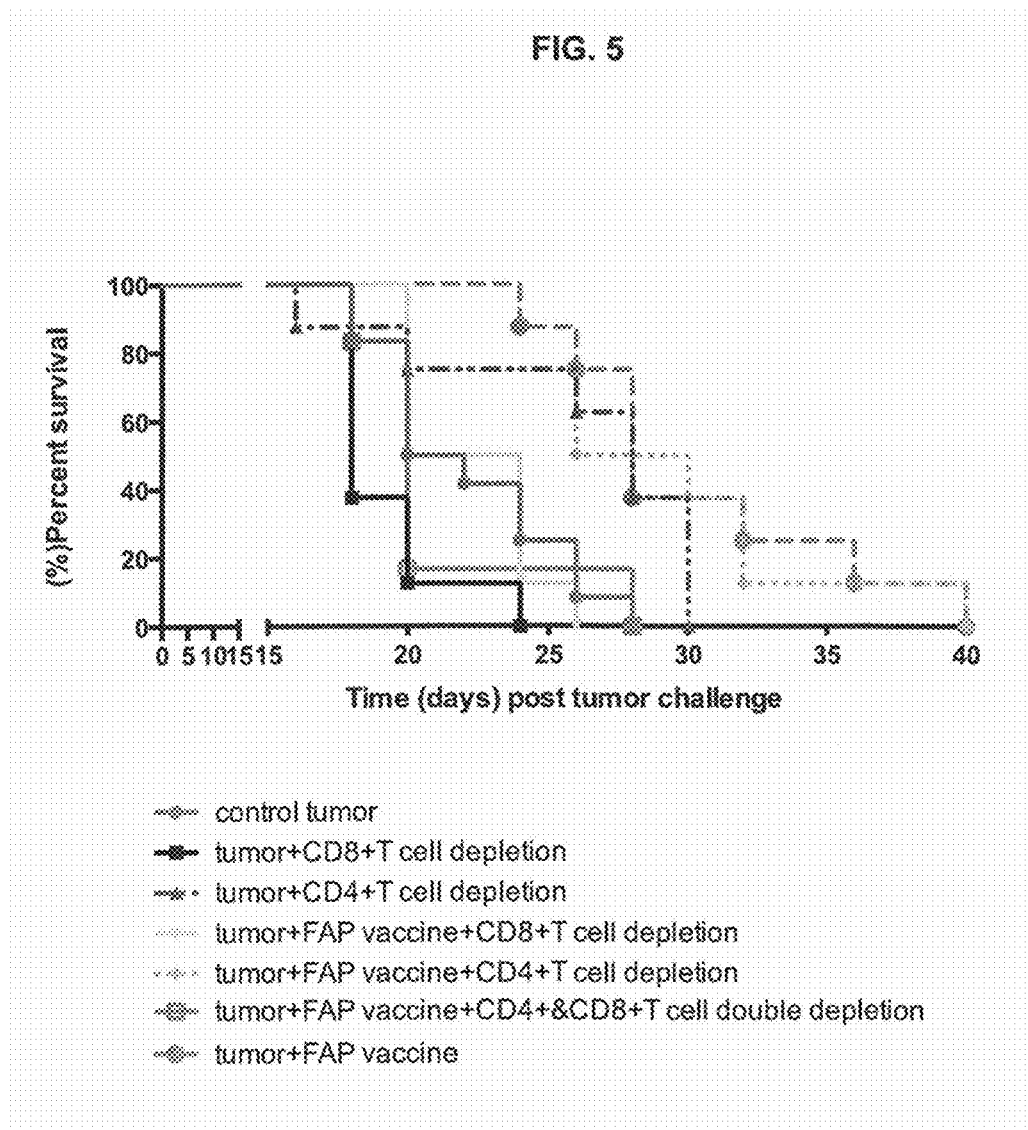

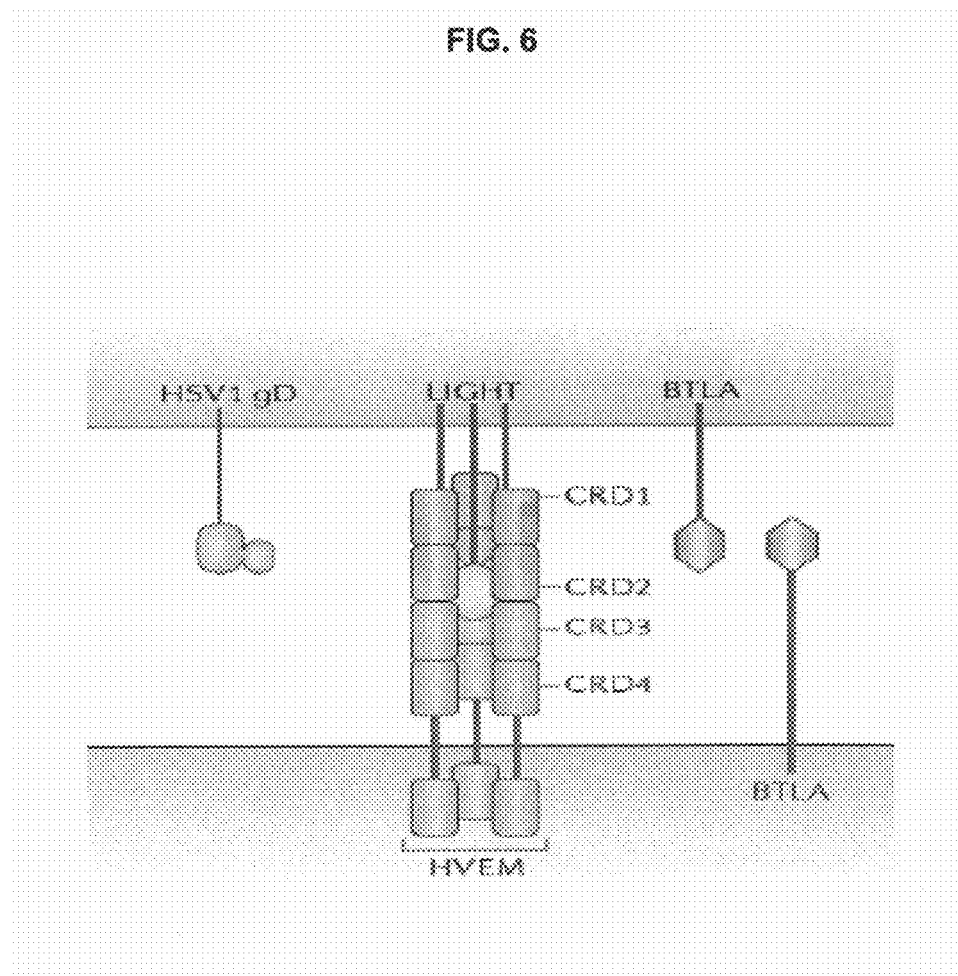

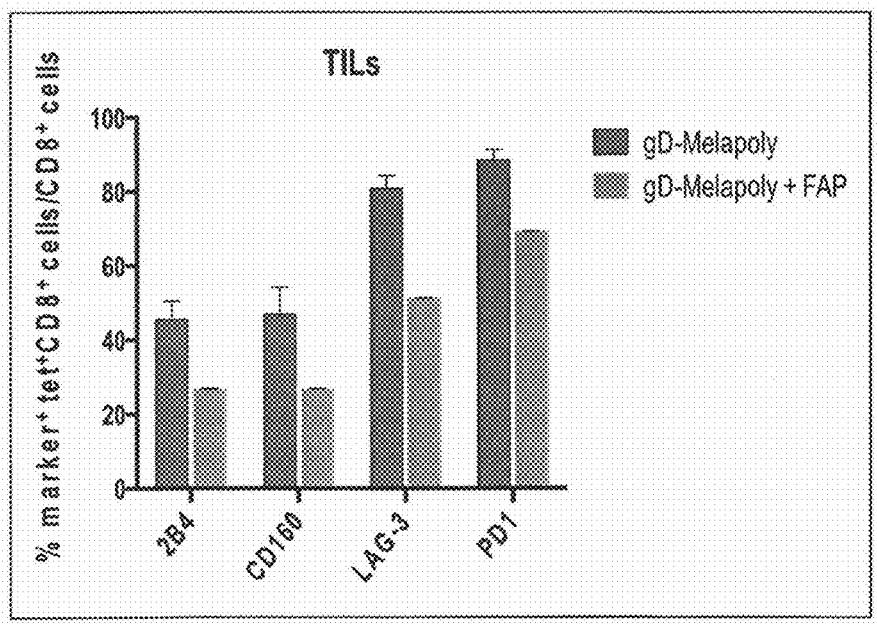

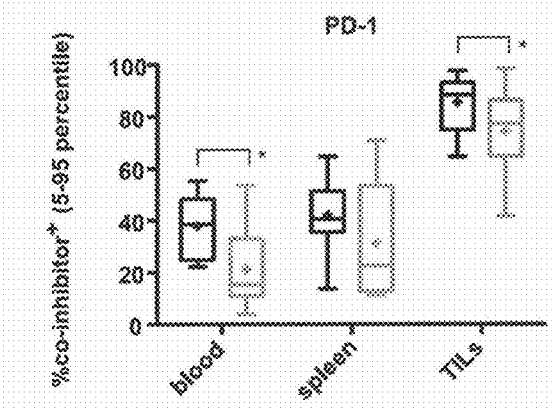 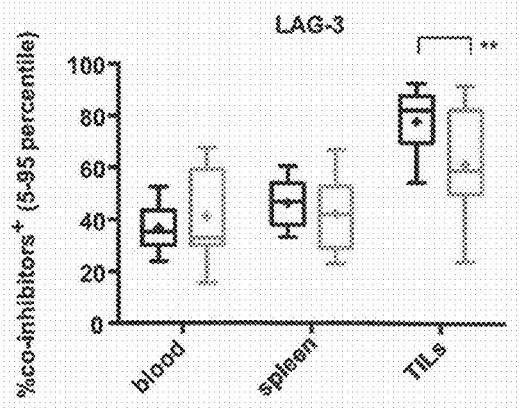

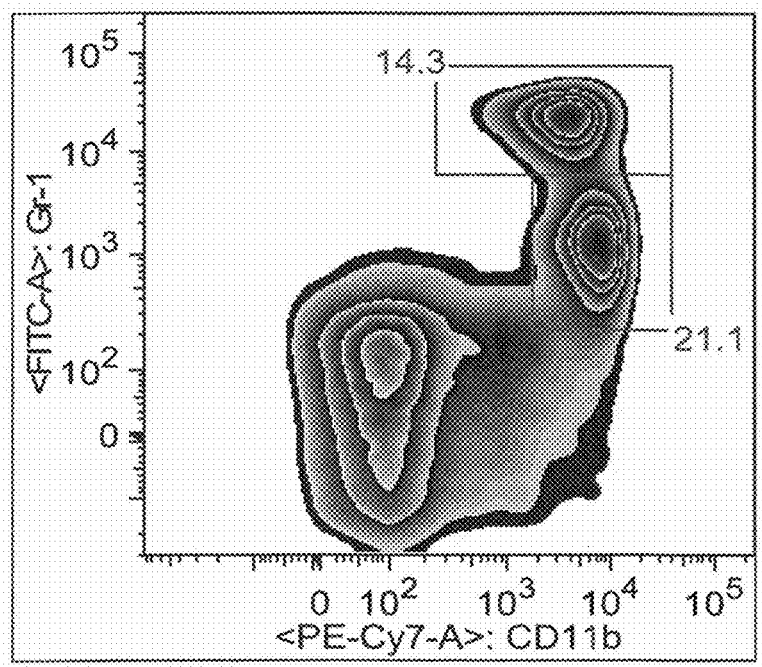

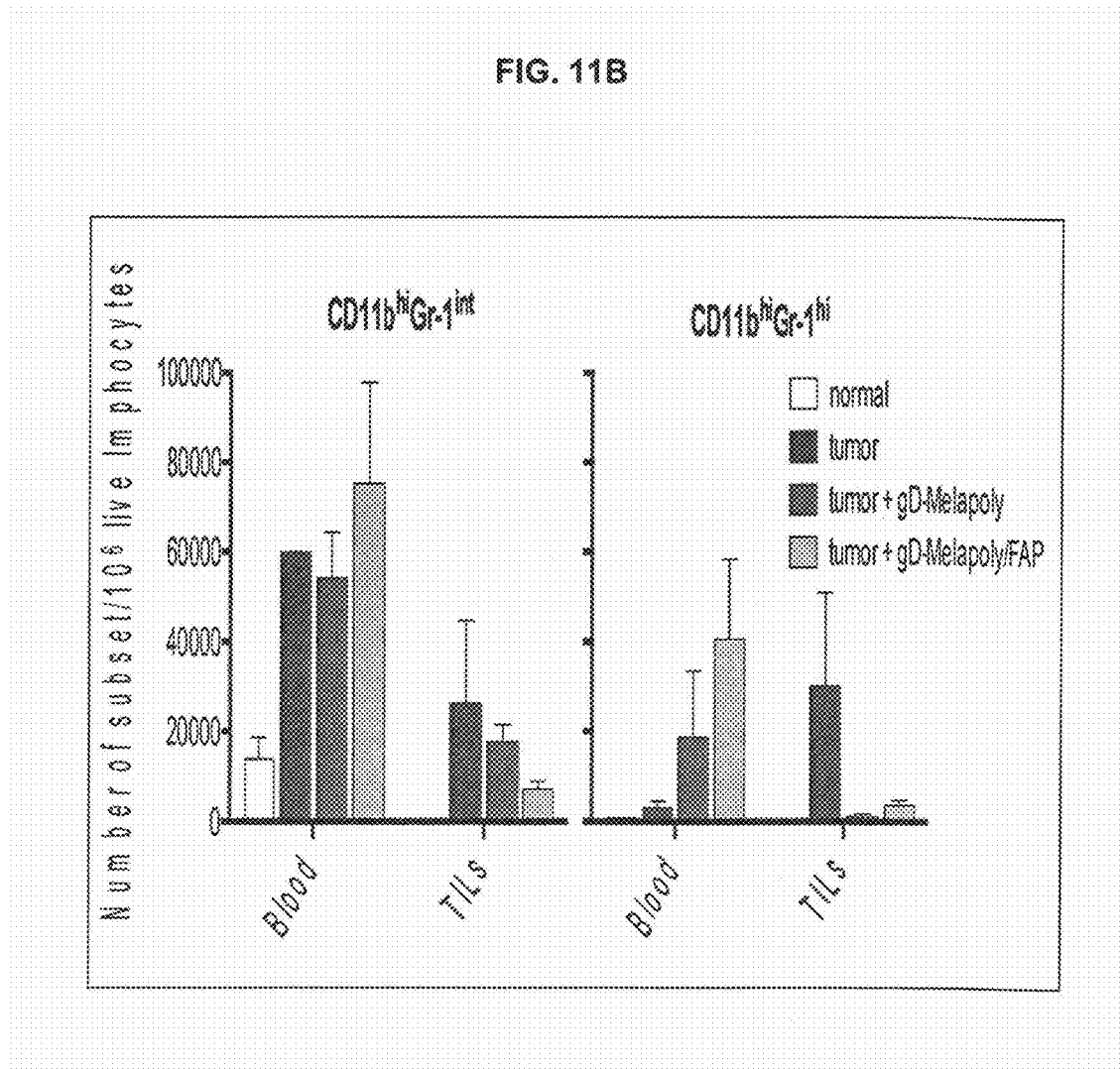

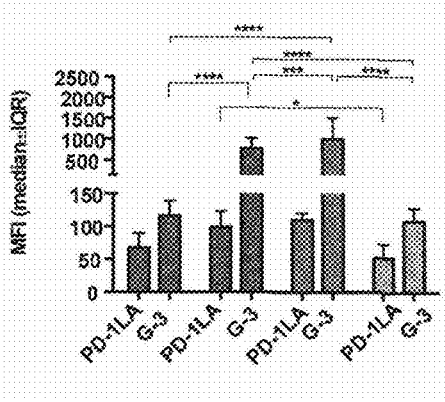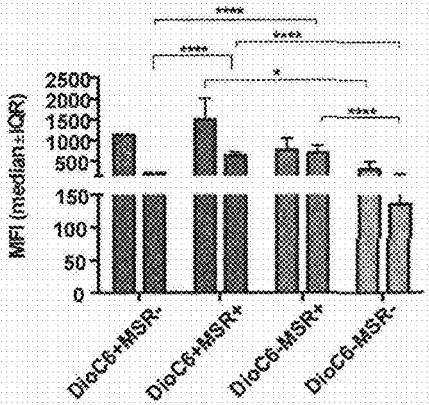

METHODS FOR TREATING CANCER BY ADMINISTRATION OF NUCLEIC ACIDS ENCODING FAP AND CANCER ANTIGENS

CROSS-REFERENCE TO RELATED APPLICATIONS

This application is a divisional application of U.S. patent application Ser. No. 14/212,099, filed Mar. 14, 2014, which claims the benefit of priority of U.S. provisional patent application No. 61/781,429, filed on Mar. 14, 2013. The disclosure of this provisional application is incorporated by reference herein.

BACKGROUND OF THE INVENTION

Low therapeutic effects of a number of cancer vaccine/immunogenic compositions are thought to be caused by various immunosuppressive elements in the tumor microenvironment, which limit the frequency and functions of induced T cells. Tumor cells themselves are not fully responsible for the immunosuppressive microenvironment. Most epithelial-derived cancers require the support of mesenchymal-derived stromal cells, which are key regulators of tumorigenesis by suppressing the immune control of tumor growth and stimulating angiogenesis, cancer cell proliferation and invasion. The specific CD8+ T cell responses against tumor antigens can be severely dampened by the prevalence of immunosuppressive receptors expressed on certain cancer cells, e.g., melanoma cells. In addition, tumor cells are capable of evading the immune pressure exerted by vaccine composition-induced immune responses due to the advantageous growth of non-targeted subpopulations, further impairing the vaccine/immunogenic composition's efficacy.

For example, melanoma is the most aggressive and lethal form of skin cancer that arises from transformed melanocytes. The incidence of melanoma has been increasing at a steady rate over the last 8 decades, and its death rate continues to rise[2]. Melanoma causes about 75% of skin cancer-related deaths. In the early stages melanoma can be cured by surgical resection, but once it progresses to the metastatic stage, it is extremely hard to treat and largely refractory to current therapies[3]. The median survival of patients with stage IV melanoma is less than 1 year.

Although promising clinical responses to the two most commonly used therapeutic methods against metastatic melanoma, i.e., chemotherapy and immunotherapy, have been seen in some patients, no therapy has been shown in a phase III trial to improve overall survival in patients with metastatic melanoma. Melanoma vaccine compositions have taken a variety of shapes and forms, ranging from whole-cell tumor preparations to recombinant viral vectors, etc. Although different types of melanoma vaccine composition candidates can induce circulating tumor antigen-specific T cells or lead to some improvement in symptoms, the clinical response rate is only in the range of 5% to 10%. However, the overall therapeutic effect of current vaccine/immunogenic composition strategies in humans is limited. Multiple factors, particularly various immunosuppressive elements in the tumor, contribute to the poor success rate of melanoma vaccine compositions. The supporting stroma of melanoma contains an abundance of tumor stromal fibroblasts (TAFs), which support melanoma growth and metastasis. It has been observed that tumor-infiltrating T cells (TILS) are defective in production of cytokines and lytic enzymes while functional antigen-specific T cells can be found in the blood of cancer patients. Another factor limiting the vaccine/immunogenic composition's efficacy is immune escape. Tumor cells are capable of evading the immune pressure exerted by vaccine/immunogenic composition due to the advantageous growth of antigen-loss variants or non-targeted subpopulations.

SUMMARY OF THE INVENTION

In one aspect, an immunogenic composition is provided that directly targets tumor or cancer stromal fibroblasts for destruction. In one aspect, the immunogenic composition comprises a first vector comprising a first expression cassette comprising a nucleic acid sequence encoding one or multiple specific antigen(s) of a cancer in which tumor progression depends on the fibroblasts expressing fibroblast activation protein (FAP). This antigen-encoding sequence is operatively linked to an expression control sequence that directs the expression of the antigen in a mammalian host cell. The immunogenic composition also includes a second vector, which comprises a second expression cassette comprising a nucleic acid sequence encoding FAP. The FAP-encoding sequence is operatively linked to an expression control sequence directing the expression of FAP in a mammalian host cell. Inclusion of a vector encoding FAP with a vector encoding a selected cancer antigen(s) provides the immunogenic compositions with an adjuvant effect which is believed to block immune-inhibitory pathways and enhance the efficacy of the immunogenic composition. In various embodiments, the cancer antigen can be a full-length cancer antigen or a polyepitope comprising a fusion of multiple cancer-associated antigens. The first and second vectors can, in one embodiment of the composition, be the same vector. In another embodiment, the first and second vectors are different.

In another aspect, an immunogenic composition, e.g., a melanoma vaccine/immunogenic composition, is provided that targets TAFs and significantly reduces the ability of tumors to evade immune elimination. This composition also combines a FAP-expressing vector with a vector expressing one or multiple melanoma antigens, melanoma associated antigens, or polyepitopes comprising a fusion of multiple melanoma-associated antigen derived epitopes.

In another embodiment, an immunogenic composition is provided that comprises a FAP-expressing vector and a vector comprising a nucleic acid sequence encoding a fusion protein in operative association with an expression control sequence directing the expression of the fusion protein in a mammalian host cell. The fusion protein comprises a polyepitope comprising two or more of hTrp-2 CD4-88, hTrp-2 CD4-237, hTrp-2 CD4-449, hTrp-2 CD8-188, hTrp-2 CD8-343, mTrp-2 CD8-363, mTrp-1 CD8-455, mTrp-1 CD8-481, mTrp-1 CD8-522, human glycoprotein hgp100 CD8-25 and Braf-V600E CD8-59, the polyepitope fused within HSV-1 gD.

In yet another embodiment, a method is provided for treating, or preventing the development of, a cancer in which tumor progression depends on the fibroblasts expressing fibroblast activation protein (FAP) in a mammalian subject. This method comprises administering any of the immunogenic compositions described herein, wherein the composition directly targets tumor or cancer stromal fibroblasts for destruction by reducing immunosuppression within the tumor microenvironment. In one exemplary embodiment, the FAP-expressing vector is combined with the vector AdC68gD-Melapoly and/or AdC6gD-Melapoly. These vectors may be administered in a prime-boost regimen.

Other aspects and advantages of these compositions and methods are described further in the following detailed description of the preferred embodiments thereof.

BRIEF DESCRIPTION OF THE DRAWINGS

FIG. 1B is a graph similar to that of FIG. 1A, but also showing an additional immunogenic composition for comparison, i.e., one comprising the adenovirus vector containing FAP with a control group (▼).

FIG. 1C is a graph showing the tumor weights of mice that received the various vaccine compositions or controls illustrated in FIG. 1B on d25 after tumor challenge. The tumor weights of mice that received the combination vaccine (gDMelapoly+FAP group) were significantly lower compared to those in both the control groups and the gDMelapoly+gD or FAP+gD vaccination group.

FIG. 2A is a bar graph showing the T cell responses of tumor cell injected mice that were immunized with (i) the adenovirus vector that expresses multiple epitopes expressed in melanoma cells linked to herpes simplex virus gD (gD-Melapoly) vaccine/immunogenic composition and (ii) gD-Melapoly and the FAP vaccine/immunogenic composition. T cell responses were revealed by intracellular staining for perforin, granzyme, IFN-γ and TNF-α. The darker bars show vaccine/immunogenic composition only, grey bars show vaccine/immunogenic composition+FAP vector. Both groups developed T cells with a similar profile to the epitopes expressed by the melanoma vaccine/immunogenic composition. Data show that the FAP vector did not increase the T cell response at early timepoints.

FIG. 2B is a bar graph of a subsequent similar experiment showing the T cell responses of tumor cell injected mice that were immunized with the vaccine/immunogenic composition compared to those of mice that also received the FAP vaccine/immunogenic composition by intracellular staining for IFN-γ and TNF-α on day 10 after vaccination. On day 10 both groups developed T cells with a similar profile to the epitopes expressed by the vaccine/immunogenic composition. These results mirror those of FIG. 2A.

FIG. 2C is a bar graph of a subsequent similar experiment showing the T cell responses of tumor cell injected mice that were immunized with the vaccine/immunogenic composition compared to those of mice that also received the FAP vaccine/immunogenic composition by intracellular staining for IFN-γ and TNF-α on day 35 after vaccination. The mice that received a combination of AdC68gD-Melapoly and AdC68mFAP vaccines showed significantly higher percentages of T cells that are IFN-γ+ or TNF-α+ only compared to those of mice that received AdC68gD-Melapoly vaccine alone. These data indicated that the addition of FAP vaccine enhances T cell polyfunctionality at later time points after tumor challenge.

FIG. 4 is a graph showing antibody responses measured at 8 week post-administration of $10^9$ viral particles (diamond), $10^{10}$ viral particles (square) and $10^{11}$ viral particles (triangle) of the vector expressing FAP to mice. Antibody responses measured in naïve mice are indicated by a cross.

FIG. 5 is a bar graph showing that the effect of the FAP-expressing vector is primarily linked to CD8+ T cells. Mice are challenged with tumor cells, vaccinated with either control vector expressing gD only or vector expressing FAP on day 3 post tumor challenge. Different groups of mice are treated with depleting antibodies depleting either CD8+/CD4+ T cell population or both from the day of tumor challenge, treated every other day for 3 times. % of survival mice is plotted vs treatment indicated in the figure.

FIG. 6 is a drawing of the molecular modeling of herpesvirus-entry mediator HVEM and its ligands (LIGHT). The ligands contact HVEM primarily through an elongated surface that spans CRD2 and CRD3. The contact region of HVEM, which is shared between HSV1gD and BTLA, is exposed.

FIG. 9A is a bar graph showing the results of TILs from the mice administered with a melanoma antigen vector only and the melanoma vector with a FAP-expressing vector analyzed upon staining for a live cell stain using antibodies to CD8, CD44, CD160, 2B4, LAG-3, PD1 and the Trp-1-tet. Cells were gated onto live CD44+, CD8+, Tet+ cells. The bar graph shows the percent of cells that highly expressed the indicated markers.

FIG. 9B is a graph showing the percentages of Trp-1455-specific CD8+ TIL cells from the three different compartments (blood, spleen and TILs) from the vaccinated mice analyzed upon staining using antibodies to PD-1 that highly expressed the co-inhibitory marker PD-1. Cells were gated onto live CD8+, CD44+, tet+ cells. The dark lines and bars represent data from mice vaccinated with gDMelapoly+control. The lighter colored lines and bars represent data from mice vaccinated with the combination vaccine. The lower the level of such co-inhibitory markers, the less exhausted and more functional are the cells, and thus more capable of killing tumor cells.

FIG. 9C is a graph generated following the protocol of FIG. 9B but using antibodies to the coinhibitory molecule LAG-3. The data is reported as for FIG. 9B. The lower the level of such co-inhibitory markers, the less exhausted and more functional are the cells, and thus more capable of killing tumor cells.

FIG. 11A is a scatterplot showing PBMCs gated onto CD4− CD8−CD45+ cells and showing the CD11b over Gr-1 stain. Squares indicate gatings for CD11b$^{hi}$Gr-1i$^{nt/hi}$ cells. The cells were isolated from normal mice and mice with large tumors. The latter had been sham-vaccinated, vaccinated with AdC68gD-Melapoly or AdC68gD-Melapoly+Ad68mFAP.

FIG. 11B is a bar graph showing numbers of the two cell populations, CD11b$^{hi}$Gr-1i$^{hi}$ and CD11b$^{hi}$Gr-1i$^{nt/}$ (+SD) in normal mice (white bars), B16Braf$_{V600E}$ tumor bearing mice that were unvaccinated (black bars), vaccinated with AdC68gD-Melapoly (intermediate gray bars) or AdC68gD-Melapoly+AdC68mFAP (light gray bars) in blood and tumors. Thus, vaccination reduced numbers of regulatory leukocytes within tumors.

FIG. 13A is a graph showing the correlation of the metabolic status of MAA-specific CD8+ T cells of FIG. 12A with their co-inhibitors' (PD-1 and LAG-3) expression in spleen. The DioC6+ or MSR+ Trp-1$_{455}$-specific CD8+ T cells showed significantly higher PD-1 or LAG-3 expression compared to those that were DioC6−MSR−. This result showed that cells with enhanced metabolic stress by increasing MMP or MROS production are also the ones that showed increased co-inhibitor expression. These cells were more 'exhausted' with reduced cytolytic functions and more prone to apoptosis.

FIG. 13B is a graph showing the correlation of the metabolic status of MAA-specific CD8+ T cells with their co-inhibitors' (PD-1 and LAG-3) expression in tumor cells of FIG. 12B.

DETAILED DESCRIPTION OF THE INVENTION

Figure 1A:
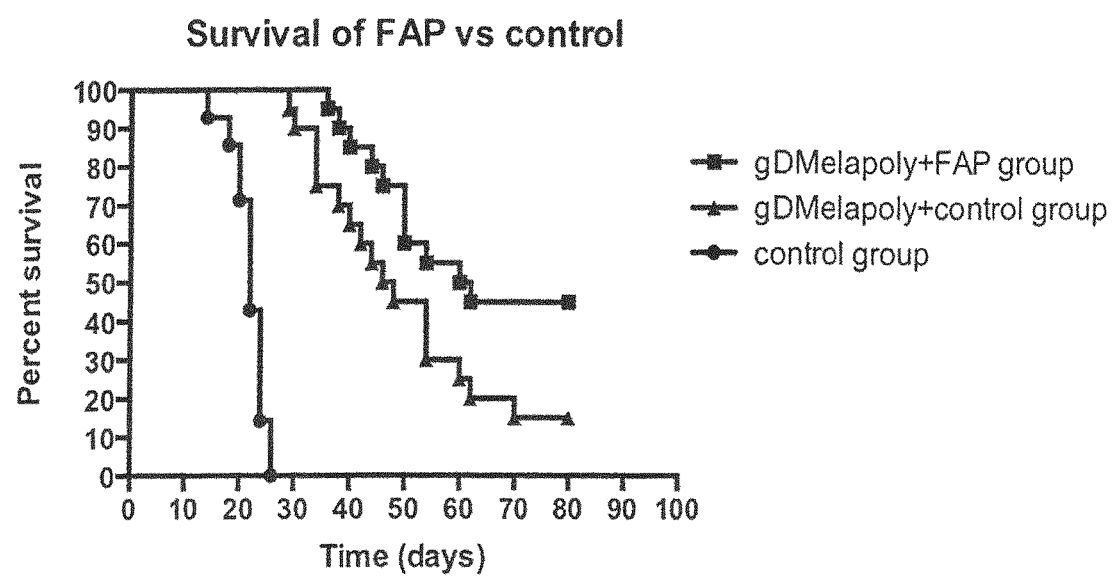
FIG. 1A is a graph showing the efficacy of the immunogenic compositions, one comprising the adenovirus vector containing FAP plus the adenovirus vector containing the melanoma polyepitope fusion (gD-Melapoly+FAP) (■), one comprising the adenovirus vector that expresses a polyepitope of multiple epitopes expressed in melanoma cells linked to herpes simplex virus gD vector (gD-Melapoly) and a control (▲) and a control only (●). The graph plots percent survival of a mouse melanoma model receiving the vaccine/immunogenic compositions after tumor cell challenge over time.

The present invention provides tumor cell targeting vaccine/immunogenic compositions and methods of use that directly reduce the tumor microenvironment's ability to suppress tumor-specific immune responses and achieve sustained tumor regression. Described herein is the anti-tumor efficacy of a combination vaccine/immunogenic composition module, which induces functional CD8+ T cells targeting both tumor cells and tumor stromal fibroblasts for destruction. In one embodiment, an immunogenic composition combines a cancer antigen-expressing vector with a vector expressing fibroblast activation protein (FAP). The expression of FAP is designed to directly impair the immune-inhibitory tumor environment, and if used in combination with a cancer-antigen expressing vector, enhances the efficacy of tumor cell-targeted vaccine/immunogenic composition. In one embodiment, the cancer antigen is fused to herpes simplex virus gD.

In one embodiment, the immunogenic compositions are designed for the treatment of melanoma. These compositions are based on a chimpanzee-derived adenoviral vector AdC68 known to induce potent CD8+ T cell responses. Such a vaccine/immunogenic composition not only expresses multiple melanoma antigens in an immunogenic form, but overcomes the low responsiveness of tumor antigen-specific CD8+ T cells.

I. DEFINITIONS

Unless defined otherwise in this specification, all scientific and technical terms used herein have the same meaning as commonly understood by to a person of skill in the fields of biology, biotechnology and molecular biology and by reference to published texts, which provide one skilled in the art with a general guide to many of the terms used in the present application. However, for clarity, the following terms are defined as follows:

The term "polynucleotide," when used in singular or plural form, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The term "polynucleotide" specifically includes cDNAs. The term includes DNAs (including cDNAs) and RNAs that contain one or more modified bases. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide of less than 20 bases, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Recombinant", as applied to a polynucleotide, means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

Typically, "heterologous" means derived from a genotypically distinct entity from that of the rest of the entity to which it is being compared. "Naturally occurring" means a sequence found in nature and not synthetically prepared or modified.

"Patient" or "subject" as used herein means a mammalian animal, including a human male or female, a veterinary or farm animal, e.g., horses, livestock, cattle, pigs, etc., a domestic animal or pet, e.g., dogs, cats; and animals normally used for clinical research, such as primates, rabbits, and rodents. In one embodiment, the subject of these methods and compositions is a human.

By "vector" is meant an entity that delivers a heterologous molecule to cells, either for therapeutic or vaccine purposes. As used herein, a vector may include any genetic element including, without limitation, naked DNA, a phage, transposon, cosmid, episome, plasmid, or a virus. Vectors are generated using the techniques and sequences provided herein, in conjunction with techniques known to those of skill in the art. Such techniques include conventional cloning techniques of cDNA such as those described in texts such as Sambrook et al, Molecular Cloning: A Laboratory Manual, $3^{rd}$ edition, 2001 Cold Spring Harbor Press, Cold Spring Harbor, N.Y., and current editions thereof, use of overlapping oligonucleotide sequences of the adenovirus genomes, polymerase chain reaction, and any suitable method which provides the desired nucleotide sequence.

By "minigene" or "expression cassette" is meant the combination of a selected heterologous gene or nucleic acid sequence of interest (e.g., an RNA/DNA sequence that expresses or encodes FAP within or without HSV-1 glycoprotein D (gD) and/or a suitable cancer antigen) and the operably linked regulatory elements necessary to drive translation, transcription and/or expression of the gene product in the host cell in vivo or in vitro. As used herein, "operably linked" sequences include both expression control sequences that are contiguous with the gene of interest and expression control sequences that act in trans or at a distance to control the gene of interest.

"Expression control sequences" include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized in the construction of the compositions and performance of the methods described herein.

By "host cell" as used herein may refer to the cell or cell line in which the recombinant vector is produced. In the alternative, the term "host cell" may refer to the target cell in which expression of the FAP and selected cancer antigen is desired.

As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

As used herein, the term "about" is defined as a variability of 10% from the reference given, unless otherwise specified.

It should be understood that while various embodiments in the specification are presented using "comprising" language, under various circumstances, a related embodiment is also be described using "consisting of" or "consisting essentially of" language. The terms "a" or "an" refers to one or more, for example, "an immunogenic composition" is understood to represent one or more such compositions. As such, the terms "a" (or "an"), "one or more," and "at least one" are used interchangeably herein.

One skilled in the art may readily reproduce the compositions and methods described herein by use of the elements described herein, which are publicly available from conventional sources.

II. IMMUNOGENIC COMPOSITIONS

The vaccine compositions or immunogenic compositions described herein employ the use of one or more vector constructs to permit expression of fibroblast activation protein (FAP) and one or more selected cancer antigens.

Fibroblast activation protein (FAP) is a type II membrane-bound glycoprotein and a member of the serine protease family that has dipeptidyl peptidase and collagenase activities. FAP is preferentially expressed on fibroblasts that are part of the stroma of some solid tumors. FAP is not expressed on epithelial tumor cells, and is also not detectable on normal fibroblasts or normal adult tissues[39]. FAP+ stromal fibroblasts are required for maintenance of the tumor microenvironment and suppress the immune response to tumors by producing stromal cell-derived factor-1 (SDF-1/CXCL12), which could attract regulatory T cells into the tumor. FAP+ stromal fibroblasts also induce random movement of effector T cells, which interferes with T cell-tumor cell interactions and hinder tumor destruction[43,44]. FAP depletion could lead to profound tumor growth inhibition. DNA vaccine/immunogenic compositions targeting FAP have been shown to inhibit tumor growth and increase tumor mice survival[37,41,42,45]. Certain nucleotide constructs expressing FAP have been proposed for therapy of tumors[40]. The nucleic acid and amino acid sequences for murine FAP used in the examples below may be obtained from NCBI database, Gene No. 14089; the nucleic acid and amino acid sequences for human FAP may be found at GenBank accession nos. U09278.1 and AAB49652.1, respectively. One of skill in the art may readily obtain the required sequences for an indicated species FAP.

Tumor stromal fibroblasts (TAFs) support melanoma growth and metastasis. TAFs differ from tumor cells by being more genetically stable[38,39]. TAFs are not transformed, but they are functionally distinguishable from resting fibroblasts in normal tissues by increased proliferation rate and differential expression of extracellular matrix components and growth factors[38,39]. One key feature is that they express FAP. The immune control of tumor growth can be directly suppressed by tumor stromal fibroblasts.

As used in the compositions and methods described herein, the term "cancer" refers to or describes the physiological condition in mammals that is typically characterized by unregulated cell growth. More specifically, as used herein, the term "cancer" means any cancer in which tumor progression depends on fibroblasts expressing FAP. In one embodiment, the cancer is an epithelial cancer. In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, and multidrug resistant cancer, or subtypes and stages thereof. In still an alternative embodiment, the cancer is an "early stage" cancer. In still another embodiment, the cancer is a "late stage" cancer. The term "tumor," as used herein, refers to all neoplastic cell growth and proliferation, whether malignant or benign, and all pre-cancerous and cancerous cells and tissues.

Cancer antigens useful in these compositions are either full-length, wild-type cancer-specific antigens or mutated cancer-specific antigens or cancer-associated antigens, or a polyepitope comprising a fusion of multiple cancer-specific or cancer-associated antigens. Cancer-specific antigens are those epitopes and proteins found on a selected specific cancer or tumor cell, and not on all cancer cells. Cancer-associated antigens are antigens that may be associated with more than one cancer or tumor cell type. Exemplary cancer-specific antigens can include, without limitation, 707-AP, alpha (a)-fetoprotein, ART-4, BAGE; b-catenin/m, b-catenin/mutated Bcr-abl, CAMEL, CAP-1, mCASP-8, CDC27m, CDK4/m, CEA, CT, Cyp-B, MAGE-B2, MAGE-B1, ELF2M, ETV6-AML1, G250, GAGE, GnT-V, Gp100, HAGE, HER-2/neu, HPV-E7, HSP70-2M HST-2, hTERT, iCE, KIAA0205, LAGE, LDLR/FUT, MAGE, MART-1, MC1R, MUC1, MUM-1, -2, -3, P15, p190 minor bcr-abl. Other suitable antigens are those listed in Parmiani G et al., "Unique human tumor antigens: immunobiology and use in clinical trials.", J Immunol. 2007 Feb. 15; 178(4):1975-97, incorporated by reference herein. See, also, texts identifying suitable antigens, such as Scott and Renner, in Encyclopedia of life Sciences 2001 Eds., John Wiley & Sons, Ltd.

Exemplary cancer-associated antigens include, without limitation, tyrosine-related protein 1 (Trp-1) and tyrosine-related protein 2 (Trp-2). The nucleic acid and amino acid sequences are the following: for human Trp 1, nucleotide accession number NM 000550, epitopes 1 and 2, and human Trp2, officially named as dopachrome tautomerase (DCT), including transcript variant 1 and 2, nucleotide accession numbers NM 001922 and NM 001129889, epitopes 1 and 2.

As one example, the cancer is melanoma. Melanoma antigens include wild-type melanoma antigens. e.g., BRAF and mutated melanoma antigens, e.g., Braf$^{V600E}$ and melanoma-associated antigens. One of the earliest and most common mutations governing melanoma initiation and progression is a point mutation (T1799A) in the Braf proto-oncogene, which encodes Braf$^{V600E}$. Braf$^{V600E}$ is a constitutively active serine kinase that elicits sustained activation of the Braf-MEK1/2-ERK1/2 MAP kinase pathway, and partially contributes to the pathophysiological characteristics of the melanoma. Braf$^{V600E}$ mutation is detected in ~65% of melanoma patients and represents a very attractive antigen for vaccine/immunogenic composition/immunogenic composition development. Although Braf$^{V600E}$ itself is a weak immunogen, one modified Braf$^{V600E}$ epitope with mutations at anchor regions to increase binding affinity to H-2D$^b$ has been developed.

Melanoma-associated (or derived) antigens Trp-1 and Trp-2 are glycoprotein, self-antigens expressed in normal melanocytes and pigmented melanomas. Both are melanogenic enzymes involved in melanin biosynthesis pathways. Numerous studies have shown that immune tolerance to these self-antigens can be broken by active immunization. In natural conditions, immune response to Trp-1 is only mediated by CD4-dependent, Th2-type autoantibodies. Some studies have shown that by introducing a series of amino acid mutations into mouse TRP1 to reduce its protein glycosylation and generate epitopes with higher H-2D$^b$ and H-2K$^b$ binding affinities, they can convert the inert syngeneic Trp1 so that can induce multi-epitope reactive CD8+ T cells cross-reactive against self-antigens. Three immunogenic Trp-1 epitopes have been identified. Immunization with lentivector expressing one modified Trp-1 has been shown to generate potent CD8+ T cell responses and anti-tumor immunity in mice. In contrast, Trp-2 has a naturally processed conserved epitope Trp-2$_{(180-188)}$ that can be recognized by both human and murine CTLs. Vaccination with TRP2 peptide-loaded dendritic cells can induce activation of high avidity TRP2-specific CTLs and lead to protective antitumor immunity against a lethal subcutaneous challenge with the B16 melanoma cell line.

An exemplary melanoma antigen useful in this invention is a modified Braf$^{V600E}$ epitope with mutations at anchor regions to increase binding affinity to H-2D$^b$. One exemplary polyepitope is a fusion protein comprising one or more of tyrosinase-related protein 1 (Trp-1), epitope 1, tyrosinase-related protein 1 (Trp-1), epitope 2, tyrosinase-related protein 2 (Trp-2), epitope 1; and tyrosinase-related protein 2 (Trp-2), epitope 2. Another exemplary polyepitope includes a cancer-specific antigen fusion with the Trp sequences identified above.

Thus, in one embodiment, an immunogenic composition comprises a vector that comprises a nucleic acid sequence encoding an antigen of a cancer or tumor and a nucleic acid sequence encoding fibroblast activation protein (FAP). In one embodiment, the composition contains a first expression cassette comprising a nucleic acid sequence encoding an antigen of an cancer or tumor, operatively linked to an expression control sequence that directs the expression of the antigen in a mammalian host cell, and a vector comprising a second expression cassette comprising a nucleic acid sequence encoding FAP operatively linked to an expression control sequence directing the expression of FAP in a mammalian host cell. In one embodiment, the cancer or cancer antigen is selected from a cancer and cancer antigen as described herein and/or the cancer is one in which cancer or tumor progression depends on the fibroblasts expressing FAP. In another embodiment, wherein two vectors or two expression cassettes are used in the immunogenic composition, the expression control sequences are the same or different.

In other embodiments of these compositions, the nucleic acid sequences encoding the cancer antigen and FAP may be presented in frame for expression as a fusion protein and thus be contained in a single expression cassette, under operative linkage to a single expression control sequence in a single vector. In an alternative embodiment, the nucleic acid sequences encoding the cancer antigen and FAP are present in a single expression cassette, linked by a splice site, under operative linkage to a single expression control sequence in a single vector.

In still other embodiments of these compositions, one or both of the nucleic acid sequences encoding the cancer antigen and/or FAP may be presented in frame with or within a protein that functions as an adjuvant that inhibits an immuno-inhibitory pathway for expression as a fusion protein. In one embodiment, the immuno-inhibitory signaling pathway in the tumor microenvironment is the B- and T-lymphocyte attenuator (BTLA)/CD160-herpesvirus-entry mediator (HVEM) pathway. Interaction between HVEM CRD1 region on antigen presenting cells and melanoma tumors with BTLA/CD160 on T cells inhibits T cell activation and leads to their functional impairment. The Herpes simplex virus (HSV) glycoprotein D (gD), through binding its N-terminus loop to CRD1 and CRD2 regions of HVEM that overlap with BTLA binding site, can block HVEM-BTLA interaction[31,32,33,34] (as shown in FIG. 6). Thus, in one embodiment, the protein that functions as an adjuvant to inhibit the pathway is HSV gD. Still other exemplary such proteins are one or more of an antibody or fragment of antibody to PD-1, PD-L1, LAG-3, CTLA-4, BTLA or CD160, among others. Vaccine/immunogenic compositions expressing antigens as fusion proteins within HSV gD or one of the other proteins identified above may induce markedly enhanced antigen-specific T cell responses, including CD8+ T cell responses to a cancer antigen.

Thus, in one embodiment, the nucleic acid sequence encoding a FAP-fusion protein may be operatively controlled by operative linkage to an expression control sequence in an expression cassette in one vector, and the nucleic acid sequence encoding a cancer antigen-fusion protein may be operatively controlled by operative linkage to an expression control sequence in an expression cassette in a different vector. In yet another embodiment, the FAP-cancer antigen fused in frame or separated by a splice site may be presented in frame with or within the adjuvant protein, in a single expression cassette in a single vector.

In one embodiment, where two vectors are employed, the two vectors can be different vectors, each containing a different expression cassette. In still another embodiment, the two vectors are the same type of vector, each containing a different expression cassette.

The FAP and/or cancer antigen sequences can be expressed in plasmid based, DNA vector systems or viral vector systems, of which many are commercially available. If two vectors are employed in an immunogenic composition, the vectors may be the same or independently selected from a variety of vectors. Suitable plasmid and viral vectors are well known to those of skill in the art and are not a limitation of the present invention. Briefly, the nucleic acid sequence encoding the FAP and/or cancer antigen sequences and/or polyepitope and/or fusion protein sequence is inserted into a vector or plasmid which contains other optional flanking sequences, a promoter, an mRNA leader sequence, an initiation site and other regulatory sequences capable of directing the multiplication and expression of that sequence in vivo or in vitro. As used herein, a vector may include any genetic element including, without limitation, naked DNA, a phage, transposon, cosmid, episome, plasmid, bacteria, or a virus. As used herein, the term vector refers to a genetic element which expresses, or causes to be expressed, the desired construct that expresses the FAP or cancer antigen in the target cell ex vivo or in vivo.

As well known in the art, a nucleotide sequence is inserted into an expression vector, transformed or transfected into an appropriate host cell and optionally cultivated under conditions suitable for expression. These procedures are generally known in the art, as described generally in Sambrook et al., cited above.

In one embodiment, the vector is a plasmid. In another embodiment, the vector is a non-pathogenic virus. In another embodiment, the vector is a non-replicating virus. In another embodiment, a desirable vector is an adenoviral vector. In another embodiment, the vector is a poxvirus. In still another embodiment, the vector is a nanoparticle.

A variety of adenovirus and other viral strains are available from the American Type Culture Collection, Manassas, Va., or available by request from a variety of commercial and institutional sources. Further, the sequences of many such strains are available from a variety of databases including, e.g., PubMed and GenBank, including type Ad5 (GenBank Accession No. M73370). The adenovirus sequences may be obtained from any known adenovirus serotype, such as serotypes 2, 3, 4, 7, 12 and 40, and further including any of the presently identified human types. Adenovirus vectors can be constructed using adenovirus DNA of one or more of any of the known adenovirus serotypes. See, T. Shenk et al., *Adenoviridae: The Viruses and their Replication*", Ch. 67, in FIELD'S VIROLOGY, 6$^{th}$ Ed., edited by B. N Fields et al, (Lippincott Raven Publishers, Philadelphia, 1996), p. 2111-2148. Recombinant adenoviruses have been described as vectors for delivery of heterologous molecules to host cells. See, e.g., U.S. Pat. No. 6,083,716, which describes the genome of two chimpanzee adenoviruses; U.S. Pat. No. 7,247,472; WO 2005/1071093, etc., as disclosing examples of adenovirus vaccine carriers. Adenovirus vectors prepared from other simian or from human adenoviruses are described in the published literature (see, for example, U.S. Pat. No. 5,240,846). Similarly adenoviruses known to infect non-human animals (e.g., simians, chimpanzees) may also be employed in the vector constructs of this invention. See, e.g., U.S. Pat. No. 6,083,716. The selection of the adenoviral source of the ITRs and the source of any other adenoviral sequences present in vector is not a limitation of the present embodiment.

Typically, an adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed in the publications referenced herein.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences.

One of skill in the art can readily construct a suitable adenovirus vector to carry and express a nucleotide sequence as described herein, e.g., an nucleic acid construct that expresses FAP and/or the selected cancer antigen in the cells by resort to well-known publications and patents directed to such viral vectors, such as those cited herein, e.g., U.S. Pat. No. 7,247,472.

Generally, each of these vectors also comprises a minigene or expression cassette as described above and/or in the examples below. These vectors also include conventional control elements that permit transcription, translation and/or expression of the nucleic acid construct in a cell transfected with the plasmid vector or infected with the viral vector. A great number of expression control sequences, including promoters which are native, constitutive, inducible and/or tissue-specific, are known in the art and may be utilized. In one embodiment, the promoter is a constitutive promoter. In another embodiment, the promoter is an inducible promoter. In one embodiment, the promoter is selected based on the chosen vector. In certain embodiments, when the vector is an adenovirus, the promoter is an RSV, U6, CMV, or H1 promoter. Still other conventional expression control sequences include selectable markers or reporter genes, which may include sequences encoding geneticin, hygromicin, ampicillin or purimycin resistance, among others. Other components of the vector may include an origin of replication. Selection of these and other promoters and vector elements are conventional and many such sequences are available (see, e.g., Sambrook et al, and references cited therein).

These vectors are generated using the techniques and sequences provided in the publications referenced herein, in conjunction with techniques known to those of skill in the art. Such techniques include conventional cloning techniques of cDNA such as those described in texts, such as Sambrook et al, cited above, use of overlapping oligonucleotide sequences, polymerase chain reaction, and any suitable method which provides the desired nucleotide sequence.

Thus, in one embodiment, using the information taught herein and publically available and known vector construction components and techniques, one of skill in the art can construct a viral vector (or plasmid) that expresses the desired construct, e.g., a nucleic acid sequence that encodes FAP and/or a selected cancer antigen.

In still other embodiments, the viral vectors or plasmids carrying the FAP and/or cancer antigen nucleic acid construct, e.g., RNA, or cDNA, are complexed or conjugated to a polymer or any other material that stabilizes the vector or assists in its targeting. Among such stabilizing polymers and materials are polyethyleneimine (PEI), which may be conjugated to the vector, resulting in the generation of nano-complexes or nanoparticles of about 50 nm, as described in Cubillos-Ruiz J R, et al, 2009 J. Clin. Invest., 119(8):2231-44, incorporated by reference herein. In another embodiment, such a stabilizing material is chitosan. In one embodiment, the vector is in a stable composition, with or without conjugation, with cholesterol. In another embodiment, the vector may be conjugated, to an antibody or fragment thereof that permits the vector to be preferentially targeted. In one embodiment, the antibody is an antibody or fragment to a desirable molecule, such as an IL7 receptor.

In one specific embodiment, an immunogenic composition directly targeting tumor stromal fibroblasts for destruction enhances the efficacy of a melanoma antigen-expressing composition by reducing immunosuppression within the tumor microenvironment. One such composition comprises an adenovirus vector comprising a nucleic acid sequence encoding a fusion protein in operative association with an expression control sequence directing the expression of the fusion protein in a mammalian host cell. The fusion protein comprises a modified Braf$^{V600E}$ epitope with mutations at anchor regions to increase binding affinity to H-2D$^b$, tyrosinase-related protein 1 (Trp-1), epitope 1, tyrosinase-related protein 1 (Trp-1), epitope 2, tyrosinase-related protein 2

Figure 7:
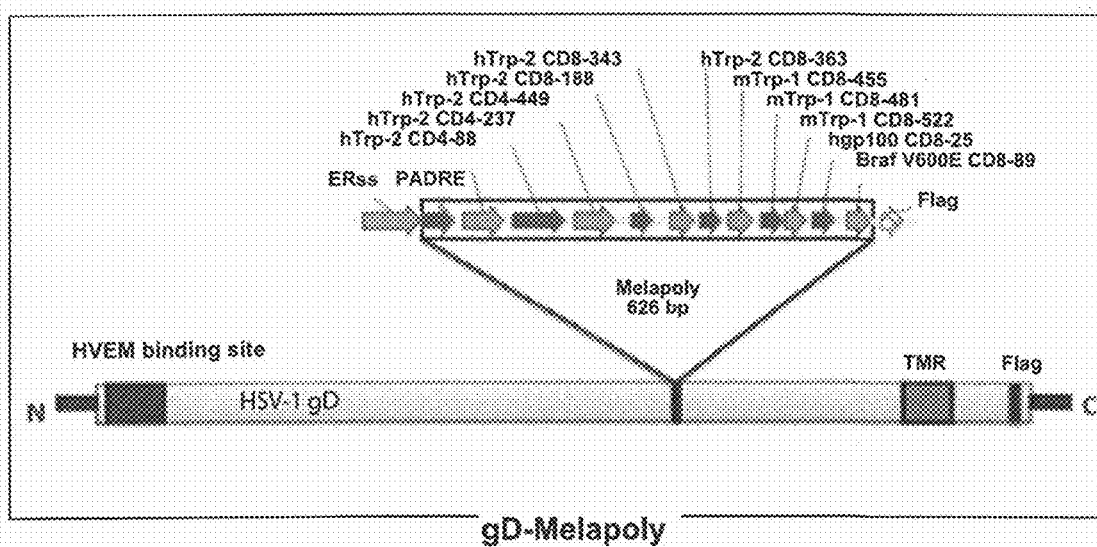
FIG. 7 is a schematic of the gD-Melapoly vaccine/immunogenic composition transgene, which is expressed in a recombinant adenovirus.

(Trp-2), epitope 1, tyrosinase-related protein 2 (Trp-2), epitope 2, and HSV gD. In another embodiment, this composition further comprises a recombinant vector comprising a nucleic acid sequence encoding expressing FAP. In another embodiment, the immunogenic composition comprises the recombinant adenovirus vectors containing the polyepitope transgene gD-Melapoly (see FIG. 7). In one embodiment, this polyepitope encoding sequence is in a simian adenovirus C68 described in Farina et al, J Virol. 2001 December; 75(23): 11603-11613. In another embodiment, this polyepitope encoding sequence is in a simian adenovirus C6 (Xiang et al, 2006 Emerging Infectious Diseases, 12(10): 1596). In still other embodiment, the polyepitope is in an expression cassette located in another selected vector.

To conquer the immunosuppressiveness exerted through BTLA/CD160-HVEM immunoinhibitory pathway, as well as minimize the frequent immune escape of tumor cells, the cancer antigens are fused within gD. The four Trp epitopes are incorporated to increase targeting, particularly to melanoma cells. In another embodiment, the immunogenic composition further comprises a recombinant adenovirus comprising a nucleic acid sequence encoding FAP, as described above.

In still another exemplary embodiment, an immunogenic composition comprises a vector comprising a nucleic acid sequence encoding a fusion protein in operative association with an expression control sequence directing the expression of the fusion protein in a mammalian host cell, wherein fusion protein comprises the polyepitope comprising hTrp-2 CD4-88, hTrp-2 CD4-237, hTrp-2 CD4-449, hTrp-2 CD8-188, hTrp-2 CD8-343, hTrp-2 CD8-363, mTrp-1 CD8-455, mTrp-1 CD8-481, mTrp-1 CD8-522, human glycoprotein hgp100 CD8-25 and Braf-V600E CD8-59, the polyepitope fused within HIV-1 gD. This composition further comprises a recombinant vector comprising a second expression cassette comprising a nucleic acid sequence encoding fibroblast activation protein (FAP) operatively linked to an expression control sequence directing the expression of FAP in a mammalian host cell.

III. METHODS

The immunogenic compositions or vaccine compositions described herein are useful in a method for treating or preventing the development of a cancer in a mammalian subject. As mentioned above, the cancer in one embodiment is a cancer in which tumor progression depends on the fibroblasts expressing fibroblast activation protein (FAP). In another embodiment, the cancer is melanoma or any of the cancers above-identified. The methods comprises administering the vaccine/immunogenic composition described herein, wherein the vaccine/immunogenic composition directly targets tumor or cancer stromal fibroblasts for destruction by reducing immunosuppression within the tumor microenvironment.

In one embodiment, the vector expressing FAP and the vector expressing the cancer antigen are the same vector and the method involves administering the composition containing that vector in a suitable pharmaceutical carrier. In another embodiment, the compositions comprise two vectors, one designed to express FAP and the other designed as described above to express the cancer antigen. The method involves administering the two vectors simultaneously in a single composition. In another embodiment, the method involves administering the two vectors in separate compositions. In one embodiment the two vectors are administered simultaneously. In another embodiment the two vectors are administered sequentially. In yet another embodiment, the two vectors are administered in a prime-boost regimen. In yet another example, the vector designed to express FAP is administered with one or more vectors designed to express one or more cancer antigens for the same cancer or tumor cells. For example, the vector designed to express FAP is administered with AdC68gD-Melapoly and ADc6gD-Melapoly, simultaneously, sequentially, or with rAd-FAP administered with rAdC68gD-Melapoly as a priming dose and rAdC6gD-Melapoly as a boosting dose. Other prime boost regimens may be designed by administering the vectors in any appropriate order.

These compositions may be administered to a patient, preferably suspended in a biologically compatible solution or pharmaceutically acceptable delivery vehicle. The various components of the compositions are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. Routes of administration may be combined, if desired. In some embodiments, the administration is repeated periodically.

The viral vectors, plasmids or nanoparticles are administered in sufficient amounts to provide sufficient levels of gene transfer and expression to express FAP and the cancer antigen and provide a therapeutic benefit without undue adverse or with medically acceptable physiological effects, which can be determined by those skilled in the medical arts. Dosages of these therapeutic reagents will depend primarily on factors such as the cancer being treated, the age, weight and health of the patient, and may thus vary among patients. For example, a therapeutically effective adult human or veterinary dosage of the viral vector or nanoparticle is generally in the range of from about 100 µL to about 100 mL of a carrier containing concentrations of from about $1 \times 10^6$ to about $1 \times 10^{15}$ virus particles, about $1 \times 10^{11}$ to $1 \times 10^{13}$ virus particles, or about $1 \times 10^9$ to $1 \times 10^{12}$ virus particles. Methods for determining the timing of frequency (boosters) of administration will include an assessment of disease response to the vector administration.

In still other embodiments, the vectors expressing FAP and the vector expressing the cancer antigen can be administered alone or in combination with various other treatments or therapies for the cancer. In another embodiment, the method further comprises, in addition to administration of the vectors expressing FAP and the cancer antigen, administering to the subject an adjunctive therapy directed toward the particular cancer being treated, which may include a monoclonal antibody, chemotherapy, radiation therapy, a cytokine, or a combination thereof. These therapies may include co-expression of T cell receptor proteins or chimeric T cell receptor proteins in the same vectors as described above or administered to the subject in separate vectors.

In still another embodiment the methods herein may include co-administration or a course of therapy also using other small nucleic acid molecules or small chemical molecules or with treatments or therapeutic agents for the management and treatment of the selected cancer. In one embodiment, a method of treatment of the invention comprises the use of one or more drug therapies under conditions suitable for said treatment. Additional immune-based or small molecules medicinal therapies can eradicate residual disease. Such combination approaches (i.e., the use of the nucleic acid constructs described and delivered herein, plus other known effective therapies for the disease or its side effects or symptoms) are anticipated to be successful in the treatment of many diseases along with the methods described herein.

It will be readily understood, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). A variety of other regimens which use the Ad capsids of the invention alone, in combination with one another, or in combination with other adenoviruses (which are preferably non-cross-reactive for neutralizing antibodies) will be apparent to those of skill in the art. Optionally, such a regimen may involve administration of rAd with capsids of other non-human primate adenoviruses, human adenoviruses, or artificial sequences such as are described herein. Each phase of the regimen may involve administration of a series of injections (or other delivery routes) with a single Ad capsid followed by a series with another capsid from a different Ad source.

The levels of immunity of the selected gene can be monitored to determine the need, if any, for boosters. Following an assessment of antibody titers in the serum or T cell responses in blood, optional booster immunizations may be desired.

Optionally, a vaccine/immunogenic composition of the invention may be formulated to contain other components, including, e.g., adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligand, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

The therapeutic levels, or levels of immunity, of the selected gene can be monitored to determine the need, if any, for boosters. Following an assessment of T cell response, or optionally, antibody titers, in the serum, optional booster immunizations may be desired. Optionally, the recombinant vectors may be delivered in a single administration or in various combination regimens, e.g., in combination with a regimen or course of treatment involving other active ingredients or in a prime-boost regimen. A variety of such regimens has been described in the art and may be readily selected.

For example, prime-boost regimens may involve the administration of a DNA (e.g., plasmid) based vector containing the cancer antigen or FAP or both, to prime the immune system to second, booster, administration with a traditional antigen, such as a protein or a recombinant virus, e.g., recombinant adenovirus carrying the sequences encoding the same or different cancer antigen. See, e.g., International Patent Publication No. WO 00/11140, published Mar. 2, 2000, incorporated by reference. Alternatively, an immunization regimen may involve the administration of a recombinant adenovirus vector to boost the immune response to a vector (either viral or DNA-based) carrying an antigen, or a protein.

In one embodiment, a method of priming and boosting an immune response to a selected cancer antigen by delivering a plasmid DNA vector carrying said antigen, followed by boosting with a recombinant adenovirus vector containing FAP or the same or different cancer antigen directed to the same cancer is described. In one embodiment, the prime-boost regimen involves the expression of polyepitope proteins from the prime and/or the boost vehicle. In another embodiment, priming may involve delivering with a first vector, plasmid or nanoparticle, followed by boosting with a second Ad vector, plasmid or nanoparticle, or with a composition containing the cancer antigen itself in protein form. In one example, the prime-boost regimen can provide a protective immune response to the cancer from which the antigen is derived. In another embodiment, the prime-boost regimen provides a therapeutic effect that can be measured using conventional assays for detection of the presence of the cancer for which therapy is being administered.

The priming composition may be administered at various sites in the body in a dose dependent manner, which depends on the antigen to which the desired immune response is being targeted. The amount or sites of injection(s) or to pharmaceutical carrier is not a limitation. Rather, the regimen may involve a priming and/or boosting step, each of which may include a single dose or dosage that is administered hourly, daily, weekly or monthly, or yearly. As an example, the subject may receive one or two doses containing between about 10 µg to about 50 µg of plasmid in carrier. A desirable amount of a DNA composition ranges between about 1 µg to about 10,000 µg of the DNA vector. Dosages may vary from about 1 µg to 1000 µg DNA per kg of subject body weight. The amount or site of delivery is desirably selected based upon the identity and condition of the mammal.

The dosage unit of the vector suitable for delivery of the antigen to the subject is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions described herein may be administered to a mammal according to the routes described above, in a sustained release formulation using a biodegradable biocompatible polymer, or by on-site delivery using micelles, gels and liposomes. Optionally, the priming step also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

One of skill in the art can readily select the appropriate and effective vaccine or therapeutic regimen using the vectors and immunogenic compositions described herein.

As demonstrated by the data described below, and in comparison to studies conducted previously using vaccine/immunogenic compositions expressing FAP only, inclusion of an antigen-expressing vaccine/immunogenic composition afforded superior protection compared to immunization with a FAP expressing vaccine/immunogenic composition only. In the examples below, an adenoviral vector expressing FAP was administered to mice that had been injected with small doses of tumor cells (a modified B16 melanoma cell line). This vector delayed tumor progression without affecting a cure. Similarly, a vaccine/immunogenic composition expressing multiple epitopes of melanoma alone again mainly caused a delay in tumor progression and only in very few mice affected complete and sustained remission. However, the combination of the FAP expressing vector with the vaccine/immunogenic composition expressing multiple epitopes of melanoma in mice that had previously been injected with melanoma cells resulted in delay in tumor progression and, more importantly, in complete remission in about 45% of mice. The combination vaccine/immunogenic composition was significantly more efficacious as compared to either vaccine/immunogenic composition given individually.

The examples below demonstrate that the FAP expressing vector does not modulate the T cell response to the antigen encoding vaccine/immunogenic composition at early timepoints following vaccination (e.g., less than 10 days). However, later timepoints, (e.g., 25-30 days following vaccination, the T cells do respond to enhance the efficacy of the vaccines, as anticipated. Without wishing to be bound by theory, the FAP expressing vector induces an adaptive immune response (both antibodies and T cells) to FAP which affects the immune-inhibitory FAP+ fibroblasts of the tumor microenvironment, thus allowing for superior elimination of tumor cells by tumor antigen-specific immune mediators of the adaptive immune system.

IV. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: The Design of Adenoviral Vaccine/Immunogenic Composition Expressing Multiple Melanoma Antigen-Derived Epitopes Fused to Herpes Simplex Virus Glycoprotein D (gD)

An adenoviral vaccine/immunogenic composition expressing multiple immunogenic melanoma antigens fused to gD can induce high frequencies of CD8+ T cells targeting melanoma cells for destruction. One embodiment of a suitable adenoviral vaccine/immunogenic composition that expresses multiple melanoma antigen-derived immunogenic epitopes fused within gD (see FIG. 7) is designed based on the chimpanzee-derived adenoviral vector AdC68 (see, e.g., U.S. Pat. No. 6,083,716). The vaccine/immunogenic composition expresses melanoma antigen derived immunogenic epitopes from mutated Braf, Trp-1, Trp-2, and gp100. Multiple epitopes are expressed to restrain melanoma immune escape. The multi-epitope "Melapoly" construct is fused to HSV gD to at least partially overcome melanoma immune inhibition.

The Melapoly expression cassette contains:
(a) an ER targeting signal sequence GMQVQIQS-LFLLLLWVPGSRG SEQ ID NO: 1,
(b) a universal T helper cell PADRE epitope AKFVAAW-TLKAAA SEQ ID NO: 2,
(c) three human CD4+T cell epitopes:

i.
    hTrp-$2_{88-102}$:
                                                SEQ ID NO: 3
    RKFFHRTCKCTGNFA, ii.
    hTrp-$2_{237-251}$:
                                                SEQ ID NO: 4
    NESFALPYWNFATGRNECDV,
    and iii.
    hTrp-$2_{449-463}$:
                                                SEQ ID NO: 5
    DQLGYSYAIDLPVSV, (d) eight CD8+ T cell epitopes from four melanoma associated antigens:
  i. a first of three modified immunogenic (dominant and subdominant) epitopes of murine Trp-1: H-$D^b$ restricted: wt 455 TAPDNLGYM SEQ ID NO: 6,
  ii. a second of three modified immunogenic (dominant and subdominant) epitopes of murine Trp-1: wt 481 IAVVNALLL SEQ ID NO: 7;
  iii. a third of three modified immunogenic (dominant and subdominant) epitopes of murine Trp-1: H-$2K^b$ restricted: wt 522: YAYDYEEL SEQ ID NO: $8^{19}$,
  iv. a first of three immunogenic epitopes of human or murine Trp-2: H-$2K^b$ restricted: hTp-$2_{180-188}$ SVYD-FFVWL SEQ ID NO: 9,
  v. a second of three immunogenic epitopes of human or murine Trp-2: hTrp-$2_{343-357}$ STFSFRNAL SEQ ID NO: 10;
  vi. a third of three immunogenic epitopes of human or murine Trp-2: H-$D^b$ restricted: mTrp-$2_{363-371}$ SQVMNLHNL SEQ ID NO: 11, vii. an immunodominant epitope of human gp100: H-D$^b$ restricted: hgp100$_{25-33}$ KVPRNQDWL SEQ ID NO: 12, and viii. a modified epitope of murine Braf: H-2D$^b$ restricted: FGLANEKSI SEQ ID NO: 13.

To generate the Melapoly expression cassette, each of the above components was separated by conventional linker sequences, synthesized, and put into a pUC57 vector backbone (Genscript catalog No. SD1176).

A pShuttle vector (Clontech) was modified to contain a CMV intron and gD resulting in vector pSH CMV-in-gD. The Melapoly expression cassette was transferred into pSH CMV-in-gD to generate pSh gD-Melapoly, which contains a CMV promoter, gD, and all the immunogenic epitopes from the expression cassette identified above.

After sequencing this construct, the multi-epitope expression cassette of pSh gD-Melapoly vector was subcloned into the E1 domain of E1-deleted AdC68 molecular clone to generate pAdC68gD-Melapoly. To determine whether using gD could overcome the immune barrier at tumor site and increase antigen-specific immune responses, a control AdC68 vector expressing the multi-epitope cassette without gD was generated using similar cloning strategies and named pAdC68Melapoly. To rescue AdC68gD-Melapoly and AdC68Melapoly vectors, the corresponding two vectors were transfected using CaCl$_2$ into HEK 293 cells, which supply Ad virus E1 in trans. Rescued virus was expanded, purified and quality controlled in vitro.

The ability of these two viral vectors to express transgenes was determined by western blot using antibody against Flag, which is incorporated at the end of each transgene.

Example 2: The Vaccine/Immunogenic Composition's Immunogenicity to Induce Tumor Antigen-Specific CD8+ T Cells Co-expression of several different immunogenic antigens in one vaccine/immunogenic composition can minimize the frequent immune escape of tumor cells. In addition, vaccine/immunogenic compositions expressing antigens as fusion proteins within gD can induce markedly enhanced antigen-specific T cell responses through disruption of the immunosuppressive BTLA-HVEM signaling pathway.

To determine the immunogenicity and therapeutic effect of this vaccine/immunogenic composition, groups of naive C57BL/6 mice were immunized intramuscularly with doses ranging from 10$^9$ to 10$^{11}$ viral particles (vps) of either AdC68gD-Melapoly or AdC68Melapoly as described above. Once the immunogenicity of these two vaccine/immunogenic compositions was confirmed in naive mice, tumor-bearing mice are similarly immunized.

Tumor-bearing mice were generated by injecting a mouse melanoma tumor cell line (B16.F10) that was modified to express mutated B-raf. The peripheral blood was harvested from immunized mice at two-week intervals, and used to determine the immunogenicity of the adenoviral vaccine/immunogenic compositions through the experiment.

The frequencies of tumor antigen-specific CD8+ T cells were measured by intracellular cytokine staining and tetramer staining. The functionality and differentiation status of these tumor antigen-specific CD8+ T cells were determined.

A. Frequencies and Kinetics of Tumor Antigen-Specific CD8+ T Cells:

Peripheral blood mononuclear cells (PBMCs) were isolated from peripheral blood samples collected two weeks after immunization. The frequencies of tumor antigen-specific CD8+ T cells in both naive mice and melanoma-bearing mice were determined through intracellular cytokine staining (ICS) and tetramer staining. To analyze the frequencies of cytokine-secreting CD8+ T cells, ICS was performed as follows. PBMCs were stimulated for 6 hours with Trp-1, Trp-2, gp100 or Braf$^{V600E}$ peptides separately, to measure specific CD8 T cell activation, or an irrelevant peptide, to measure background cytokine secretion. Cells were stained for CD8, fixed and permeabilized, and stained for IFN-γ. Samples were analyzed by flow cytometry. Results were presented as the proportion of CD8+IFN-γ+ cells per total CD8 cells. To analyze Trp-1- and Trp-2-specific tetramer frequencies, PBMCs were stained for CD8, CD44, mouse Trp-1$_{455}$-specific CD8+T cell tetramer: MHC I H-D$^b$ carrying the TAPDNLGYM (amino acids 1-9 of SEQ ID NO: 6) peptide and mouse Trp-2$_{180}$-specific CD8$^+$ T cell tetramer: MHC I H-K$^b$ carrying the SVYDFFVWL SEQ ID NO: 9 peptide. Data were presented as the percentage of CD8+tet+ cells over the whole CD8$^+$ T cell population. These tests were repeated every two weeks to determine the kinetics of tumor antigen-specific CD8+ T cell responses respectively.

B. Functionalities of Tumor Antigen-Specific CD8+ T Cells:

1) Effective Factors

To determine the functional status of these tumor antigen-specific CD8+ T cells, their ability to secrete effective factors in both immunized normal mice and immunized melanoma-bearing mice was analyzed by ICS every two weeks. Briefly, PBMCs and splenocytes were stimulated with Trp-1, Trp-2, gp100 and Braf peptides. Then the cells were stained for CD8 and intracellular factors: IFN-γ, TNF-α, IL-2, CD107a/b, granzyme B, perforine, MIP-1α. As a control, PBMCs and splenocytes from the same mouse were stimulated with an irrelevant peptide. The percentage of CD8+ T cells producing each factor were measured by flow cytometry. The results were compared between normal mice and melanoma-bearing mice which both were vaccinated to determine whether the functionalities of induced CD8+ T cells were impaired in melanoma-bearing mice.

2) Migration to Tumor Site

Once the specific CD8+ T cells are induced, one prerequisite to exert their killing function is to migrate to tumor site. Therefore, the infiltration of tumor-specific T cells to melanoma sites was determined. Two groups of tumor-bearing mice were injected with the optimized dose of either gD or non-gD vector. Once tumor developed, mice were euthanized and melanomas were excised. Tumor-infiltrating lymphocytes (TILs) from melanoma tissue were isolated to analyze the frequencies and functionalities of Trp-1-, Trp-2-, gp100- and Braf-specific CD8+T cells, by ICS or tetramer staining.

C. Differentiation Status of Tumor Antigen-Specific CD8+ T Cells:

One devastating feature of tumor microenvironment is to reduce the responsiveness of specific CD8+ T cells by leading to T cell exhaustion[50]. To determine whether the vaccine/immunogenic composition can conquer this immunosuppressive barrier, the differentiation status of tumor antigen-specific CD8+ T cells was determined, especially their expression of exhaustion markers. Groups of normal and tumor-bearing mice were immunized with the optimized dose of two vectors. PBMCs and TILs were collected from each group of mice and stained for CD8+, Trp-1 and Trp-2 tetramers, activation markers CD44, CD69, CD62L and exhaustion markers PD-1, BTLA, CD160 and LAG-3. The results were analyzed as the expression of activation and exhaustion molecules on total CD8+ T cells or Trp-1/2-specific CD8+ T cells (CD8+tet+) in peripheral blood and melanoma tissue.

D. Frequencies of Regulatory T Cells (Tregs) at Tumor Site:

The presence of Tregs at tumor site is a key factor that inhibits the function of infiltrated tumor-reactive effector T cells[26]. To determine whether the tumor cell targeting vaccine/immunogenic composition could reduce the frequencies of Tregs in melanoma tissue, TILs isolated at different time points after immunization were analyzed. TILs from untreated tumor-bearing mice at different time points after tumor induction served as negative control. The Tregs were defined as CD4+CD25+Foxp3+ cell population. Data were presented as the percentage of CD4+CD25+Foxp3+ cells over the CD8+CD44+ effector T cell population. The ratio of Treg to effector CD8+ T cells at tumor site is one indicator of whether this vaccine/immunogenic composition reduces the immunosuppressiveness of tumor microenvironment.

Example 3: The Vaccine/Immunogenic Composition's Therapeutic Effect

To determine the capacity of this tumor-targeting vaccine/immunogenic composition to kill established tumors and therapeutic effect of this vaccine/immunogenic composition, the tumor status and survival time of vaccinated melanoma-bearing mice was measured and compared to those of control mice. Groups of tumor-bearing mice were immunized with optimized doses of either gD or non-gD vaccine/immunogenic composition; one group of tumor-bearing mice was left untreated. The tumor size in all mice was recorded every other day by measuring 2 perpendicular diameters. Mice were sacrificed upon signs of heavy tumor burden (i.e., >10% body weight) and ulceration of the skin[51]. The survival time before euthanasia was compared between different groups. Necropsy was performed in all mice upon euthanasia. The tumor status was determined by observation, measuring the tumor volume and weight. Also tumor sections were prepared for H&E staining. The overall therapeutic effect of the vaccine/immunogenic compositions was analyzed by comparing tumor status, and survival time among mice from vaccinated groups and control group, to see if the differences in parameters reach statistical significance.

It is anticipated that if the generated adenoviral vectors are functional, AdC68gD-Melapoly vector and AdC68Melapoly vector express transgenes at a similar level, since both transgenes are under the control of same enhancer and CMV promoter. High frequencies of transgene-specific CD8+ T cells were observed on day 14 after immunization in normal mice, after which the responses went down overtime but failed to undergo a pronounced contraction as is typical for adenoviral vector induced T cell responses. The immune responses induced by gD-antigen vector were higher than responses induced by dose-matched non-gD vector. In the tumor-bearing mice, the frequencies of CD8+ T cells were relatively lower compared to those in normal mice, since the immunosuppressive environment in tumor-bearing mice inhibits the induction of potent T cell responses.

It is expected that specific CD8+ T cells induced in naive mice possess potent capacity to secrete effective factors two weeks after immunization. The frequencies of factor secreting cells induced in melanoma-bearing mice are expected to be lower. In terms of tumor infiltrating T cells, the frequencies of transgene-specific TILs may be higher compared to those in peripheral blood of same mouse, and these TILs may markedly upregulate exhaustion markers expression overtime. Tregs/$T_{effector}$ ratios at tumor site of gD vector treated mice are expected to be lower compared to control tumor-bearing mice. The time point at which melanoma mice are immunized after tumor cell challenge may influence the vaccine/immunogenic compositions-associated immune responses and therapeutic effects. If the tumor mice are treated at early time points when the tumor are very small, specific immune responses that can be triggered and the therapeutic effects are much better compared to results generated from vaccinated mice with more established tumors.

Overall significantly enhanced tumor antigen-specific CD8+ T cell responses were induced by AdC68gD-Melapoly vaccine/immunogenic composition, and this vaccine/immunogenic composition achieved partial therapeutic effect to kill melanoma and elongate the survival time of melanoma mice. Nevertheless, the vaccine/immunogenic composition did not necessarily cure mice completely, especially if it was given to mice with advanced tumors.

A transplantable tumor model was used to test vaccine/immunogenic composition efficacy. Alternative models based on tumor-prone mice were also used. For the transplantable tumor model, a modified B16 tumor cell line is transduced with BrafV$^{600E}$. As both Trp-1 and Trp-2 are overexpressed in B16 tumor cells, this modified cell line expresses all three tumor-targeting antigens. Tumor cells were implanted into naive C57BL/6 mice via either i.v. or s.c. route, followed by 5-7 days of time for tumor establishment either in the lung or subcutis before vaccination[29]. All other early experiments were performed in the same way in this tumor model.

Example 4: The Anti-Tumor Capacity of Combined Adenoviral Vaccine/Immunogenic Compositions Against Both Tumor Stromal Fibroblasts and Melanoma Cells Tumor stromal fibroblasts express selectively the fibroblast activation protein (FAP), which is not expressed by normal fibroblasts or normal adult tissues. FAP+ stromal fibroblasts suppress the immune response to tumors by attracting regulatory T cells into the tumor and interfering with T cell-tumor cell interaction. Combining adenoviral vaccine/immunogenic composition directly targeting tumor stromal fibroblasts for destruction enhances the efficacy of the melanoma antigen-expressing vaccine/immunogenic composition by reducing immunosuppression within the tumor microenvironment. Adenoviral vaccine/immunogenic composition expressing murine full-length FAP was constructed and its immunogenicity determined in both naïve and melanoma mice. The efficacy of this vaccine/immunogenic composition to destruct tumor stromal fibroblasts is determined by immunofluorescent staining of tumor material and in vitro assays. To determine the immunogenicity of combined vaccine/immunogenic compositions, the frequencies and functionalities of specific CD8+ T cell responses were measured against both FAP and different tumor antigens after this combination treatment in melanoma mice and the results are compared with single vaccine/immunogenic composition treatment. Finally, to determine the therapeutic effect of combined vaccine/immunogenic compositions, tumor status and survival time of mice treated with the combination vaccine/immunogenic compositions were measured.

Together, these experiments demonstrated that this novel vaccine/immunogenic composition combination strategy enhances anti-tumor efficacy and increased the success of eliminating melanoma when compared to traditional vaccine/immunogenic composition candidates.

Stromal compartment contributes greatly to tumorigenesis and invasion. Stromal cells play a pivotal role in the complicated communication network with cancer cells and immune cells to provide the appropriate tumor microenvironment for neoplastic cell expansion and metastasis. In addition, tumor-stromal fibroblasts (TAF), which are important components of stromal cells, can synthesize VEGF, TGF-β, and IL-10 and contribute to the local immunosuppressive environment[38]. As immune suppression within the tumor microenvironment is a major determinant of the poor outcome of therapeutic vaccination, developing cancer vaccine/immunogenic composition targeting TAF for destruction complements therapies directed against cancer cells[43]. FAP has recently gained attention as a novel vaccine/immunogenic composition target for TAF based on its highly restricted expression and structurally defined proteolytic activity. Previous studies have shown that an effective CD8+ T cell response against FAP could be induced that significantly suppressed epithelial tumor growth[40,41,42]. Therefore AdC68 vector expressing murine full-length FAP was constructed, and both its immunogenicity and melanoma stroma killing capacity were determined in a melanoma mouse model. TAF and melanoma cell targeting vaccine/immunogenic compositions were combined to treat tumor-bearing mice. The immunogenicity and therapeutic effect of combined vaccine/immunogenic composition treatment was determined.

A. Adenoviral Vaccine/Immunogenic Composition Expressing Murine Fibroblast Activation Protein (FAP)

A fully sequenced FAP transgene was excised from the pcDNA3 vector (Invitrogen) expressing murine full-length FAP (pcDNA3-mFAP) (provided by Ellen Pure, Wistar Institute). This sequence was inserted into the pShuttle CMV intron (pSh CMV-in) expression vector (GenBank No. AF334399) and from there into the molecular viral AdC68 clone (Farina et al, J Virol. 2001 December; 75(23): 11603-11613). The resulting plasmid is pAdC68mFAP, from which the AdC68mFAP virus was rescued. FAP expression by the recombinant AdC68 vectors was determined by western blot using rabbit polyclonal antibody against FAP.

B. The Immunogenicity and Tumor Stromal Fibroblasts Killing Capacity of FAP Targeting Vaccine/Immunogenic Composition Alone Groups of naive C57BL/6 mice were immunized i.m. with doses ranging from $10^9$ to $10^{11}$ viral particles (vps) of AdC68mFAP. Once this composition's immunogenicity was confirmed in naive mice, it was tested for immunogenicity and functionality in tumor-bearing mice. The peripheral blood is sampled after vaccination at two-week intervals, and was used to determine the immunogenicity of this FAP targeting vaccine/immunogenic composition.

1) Frequencies and Kinetics of FAP-Specific CD8+ T Cells:

PBMCs were isolated from peripheral blood samples. The frequencies of FAP-specific CD8+ T cells in both naive mice and transgenic melanoma mice were determined by ICS. PBMCs were stimulated for 5 hours with fibroblasts MHC class I or II binding peptides of murine FAP. ICS was repeated every two weeks to determine the kinetics of FAP-specific CD8+ T cell responses. The results were compared between normal and melanoma mice groups.

2) Functionalities of FAP-Specific CD8+ T Cells:
a) Effective Factors:

To determine the functional status of FAP-specific CD8+ T cells, their ability to secrete effective factors in both immunized naive and melanoma mice was analyzed by ICS every two weeks. The cells were stained for IFN-γ, TNF-α, IL-2, CD107a/b, granzyme B, perforine, MIP-la. The percentage of CD8+ T cells producing each factor was measured. The results helped determine whether the functionalities of induced CD8+ T cells were impaired in melanoma mice.

b) Migration to Tumor Sites:

On day 14 after vaccination, melanoma mice are euthanized and tumors are excised to isolate TILs. The frequencies and functionalities of FAP-specific TILs in melanoma tissue are analyzed after immunization, by ICS and stained for effective factors IFN-γ, TNF-α, perforin and granzyme B.

3) Generation of FAP-Specific Antibodies:

This AdC68 mFAP vaccine/immunogenic composition may also activate specific B cells to secrete FAP-specific antibodies. These antibodies could help kill FAP+ tumor stromal fibroblasts in melanoma tissue via antibody-dependent complement activation or antibody-dependent cell-mediated cytotoxicity (ADCC). To determine the presence of FAP-specific antibody and measure its concentration in serum, an Enzyme-linked immunosorbent assay (ELISA)[35] was performed. Briefly, serum was collected from both immunized naive and tumor-bearing mice on day 14 and 28; serum samples from same age untreated naive and tumor-bearing mice were used for background analysis. ELISA plate was coated with recombinant murine FAP ectodomain protein (mFAP-ECD)[52]. Recombinant mFAP-ECD protein (736 amino acids of the ectodomain) was generated by transfecting HEK293 cells with a suitable expression vector. The recombinant protein contains a Flag-tag to allow for its purification by affinity chromatography. The purified protein was used to coat ELISA plates (~200 ng of protein per well in 96-well plates). Plates were blocked and incubated with serial dilutions of mouse sera.

4) Tumor Stromal Fibroblasts Killing Capacity:

The efficacy of FAP-targeting vaccine/immunogenic composition to lyse tumor stromal fibroblasts is determined. One group of tumor-bearing mice is immunized with the optimized dose of AdC68 mFAP; another group is immunized with an Ad vector expressing an irrelevant antigen serving as negative control. Day 14 and 28 post vaccination, mice from both groups are euthanized; tumors are harvested and paraffin embedded. Four-micron sections are cut and stained with H&E. Immunohistochemistry staining is performed using antibody against FAP. Immunofluorescent staining is performed using antibodies against FAP and alpha-smooth muscle actin (α-SMA). α-SMA is a marker for myofibroblast, which is a cell type always found to be FAP positive at tumor site[43]. The results analyzed by comparing the presence of FAP-expressing fibroblasts in tumor samples from vaccinated and sham-vaccinated melanoma mice.

C. The Immunogenicity and Efficacy of Combined Vaccine/Immunogenic Compositions Expressing Tumor Antigens and FAP 1. Early Timepoint Tests and Evaluation The capacity of combined vaccine/immunogenic composition treatment to induce tumor antigen-specific CD8+ T cell responses was analyzed as well as the function of these T cells. To test this, a group of tumor-bearing mice was immunized with an optimized dose of AdC68 gD-Melapoly and an optimized dose of AdC68mFAP. A control group of tumor mice was given the same dose of gD-Melapoly vector, but combined with AdC68 empty vector. Another group received AdC68mFAP (+empty vector). Every two weeks, PBMC samples were collected from each group of mice and subjected to measure the frequencies of tumor antigen-specific CD8+ T cells, their ability to secrete effective factors, and their differentiation status by ICS and tetramer staining. The in vivo killing capacity of these specific CD8+ T cells were compared. Tumor growth was monitored.

Figure 8A:
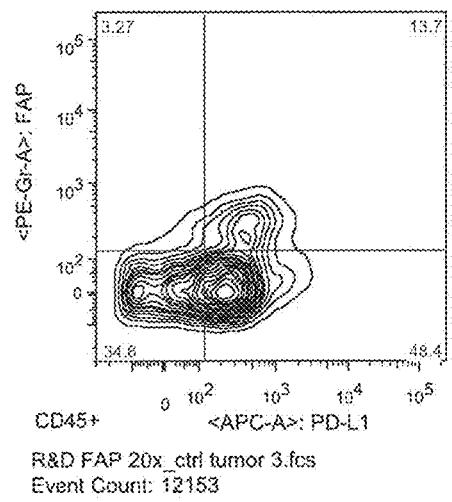
FIG. 8A is a flow cytometry two dimensional contour map of a mouse tumor. Mice were challenged with $B16Braf_{V600E}$ cells ($5\times10^4$). Three days later they were vaccinated with $10^{11}$ vp of AdC68gD (control). Tumors were excised once they exceeded 1 cm in diameter and digested with collagenase. Single cells were stained with a live cell dye PE-Gr-A, and antibodies to CD3, CD14, CD19, FAP(R&D), CD45 and PD-L1. Cells were analyzed by flow cytometry. Blots were gated on live, CD3−, $CD14^-CD19^-CD45^{int}$ cells. This blot shows FAP over PD-L1 stain
Figure 8B:
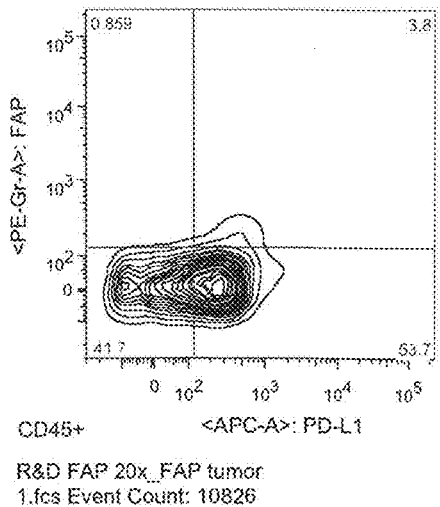
FIG. 8B is a flow cytometry two dimensional contour map of a mouse tumor. Mice were challenged with $B16Braf_{V600E}$ cells ($5\times10^4$). Three days later they were vaccinated with $10^{11}$ vp of AdC68FAP and AdC68gD (FAP plus the control). Tumors were excised and treated as described in FIG. 8A. Single cells were stained, analyzed and blots gated as described in FIG. 8A. This blot shows FAP over PD-L1 stain.

Inclusion of the AdC68mFAP vector into the vaccination protocol did not affect the magnitude or the cytokine secretion patterns of AdC68gD-Melapoly-induced CD8+ T cells at these early timepoints (not shown). This is not surprising as both vaccines were given together and any effect of FAP-induced immune responses would occur after the initial stage of MAA-specific T cell activation. FAP vaccination did reduce numbers of CD3$^-$CD14$^-$CD19$^-$CD45$^{int}$FAP$^+$PD-L1$^+$ cells within the tumors (See FIGS. 8A and 8B). This cell population may reflect FAP$^+$ fibroblasts that through expression of PD-L1 contribute to subversion of the immune responses.

TILs from the mice were analyzed upon staining for a live cell stain using antibodies to CD8, CD44, CD160, 2B4, LAG-3, PD1 and the Trp-1-tet. Cells were gated onto live CD44+, CD8+, Tet+ cells. The bar graph of FIG. 9A shows the percent of cells that highly expressed the indicated markers. FAP vaccination was shown to reduce expression of immunoinhibitory molecules on MAA-specific CD8+ T cells (FIG. 9A) suggesting better preservation of functions.

Figure 10A:
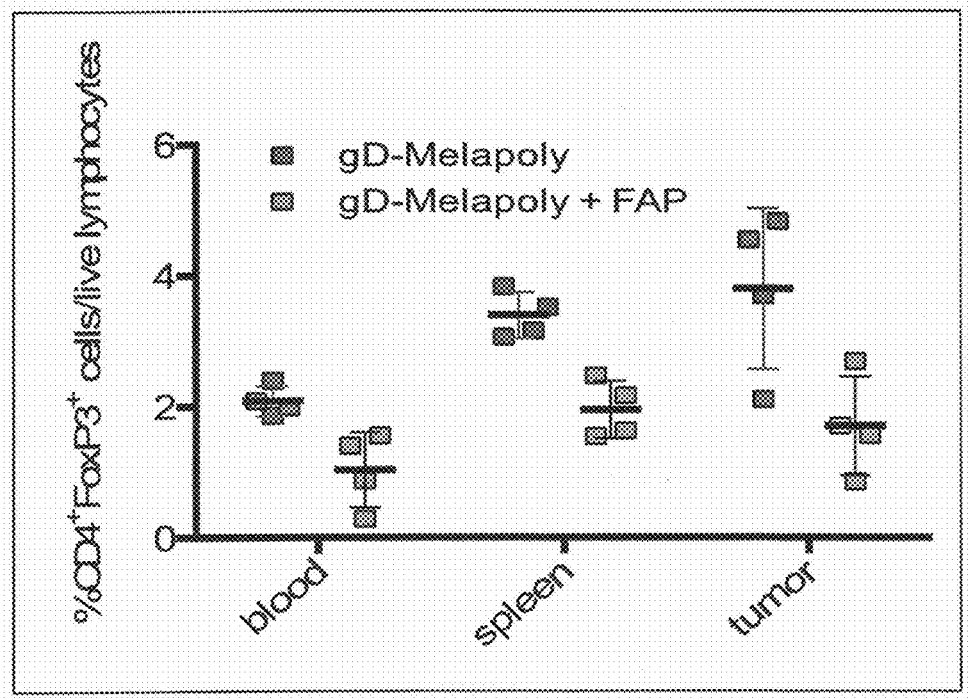
FIG. 10A is a graph showing the percentage of CD4+FoxP3+ cells over all live lymphocytes in mice administered with a melanoma antigen vector only and the melanoma vector with a FAP-expressing vector. Lymphocytes from blood, spleen and tumors from the mice vaccinated with AdC68gD-Melapoly alone (dark gray) or combined with AdC68mFAP (lighter gray) are analyzed upon staining with a live cell stain and antibodies to CD4 and FoxP3. At the time of necropsy when tumors exceed 1 cm of diameter, mice receiving both vectors have lower percentages of CD4+FoxP3+ cells in blood, spleens and tumors as compared to mice that are only vaccinated with AdC68gD-Melapoly.

Some preliminary studies were conducted to assess regulatory CD4$^+$CD25$^+$FoxP3$^+$ cells in vaccinated tumor-bearing or non-tumor-bearing mice. Lymphocytes from blood, spleen and tumors from the mice vaccinated with AdC68gD-Melapoly alone or combined with AdC68mFAP were analyzed upon staining with a live cell stain, and antibodies to CD4 and FoxP3. The graph of FIG. 10A shows percentages of CD4$^+$FoxP3$^+$ cells over all live lymphocytes. Mice vaccinated with AdC68gD-Melapoly+AdC68mFAP showed, at the time of necropsy when tumors exceeded 1 cm of diameter, lower percentages of CD4$^+$FoxP3$^+$ cells in blood, spleens and tumors as compared to mice that were only vaccinated with AdC68gD-Melapoly.

Figure 11C:
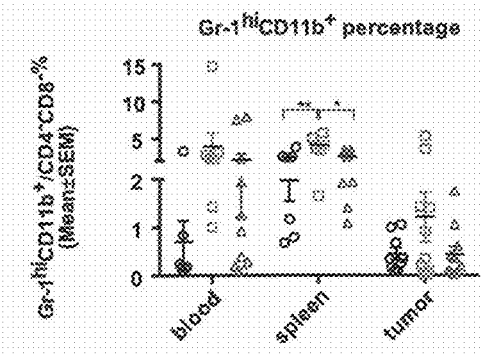
FIG. 11C is a graph showing the percentages of Gr-1$^{hi}$CD11b+ cells from blood, spleen and tumors of mice vaccinated with AdC68-gD only (○, control group), AdC68gD-Melapoly combined with AdC68gD (□), or AdC68gD-Melapoly combined with AdC68mFAP (Δ), at the time of necropsy (when tumors exceeded 1 cm of diameter). The cells were analyzed upon staining with a Gr-1 stain and antibodies to cell lineage markers, e.g., CD4 and FoxP3.

Cells were isolated from normal C57Bl/6 mice and mice with large tumors. The latter had been sham-vaccinated, vaccinated with AdC68gD-Melapoly or AdC68gD-Melapoly+Ad68mFAP. However, blood of normal C57Bl/6 mice contained modest numbers of CD11b$^{hi}$Gr-1$^{int}$ immature monocytes. They are also called myeloid-derived suppressor cells (MDSCs) and have been implicated to suppress CD8+ T cells in cancer-bearing hosts[34-36]. MDSCs were found to be more common in blood (and spleen, not shown) of mice bearing large B16Braf$^{V600E}$ tumors. They were also detected within tumors. FIGS. 11A and 11B show the results for blood and tumors. Vaccination with AdC68gD-Melapoly has no effect on MDSCs in blood but reduces their numbers (and frequencies) within tumors especially if the vaccine is combined with AdC68mFAP. Interestingly a small population of CD11b$^{hi}$Gr-1$^{hi}$ cells was detected in blood of tumor-bearing mice. In blood (and spleen), this population was markedly increased upon AdC68gD-Melapoly vaccination especially if combined with AdC68mFAP vaccination. CD11b$^{hi}$Gr-1$^{hi}$ cells were enriched in tumors of non-vaccinated mice. Their numbers were lower within tumors of vaccinated mice. CD11b$^{hi}$Gr-1$^{hi}$ cells have been reported previously in tumor-bearing mice[37-39]. Their immunosuppressive functions are limited to some tumors and only if cells are present at high numbers.

2. Updated Test Results, Later Timepoints and Further Analysis

Figure 3A:
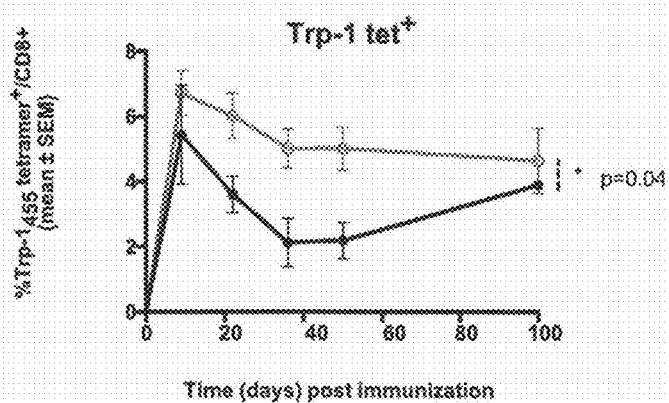
FIG. 3A is a graph showing the kinetics of MAA-specific $CD8^+$ T cell responses in the blood of mice that received AdC68-gDMelapoly vaccine with (light circle) or without (dark circle) AdC68mFAP vaccine over time. These mice were vaccinated 3 days after they were challenged with $B16Braf_{V600E}$ tumor cells. The responses were measured by Trp-$1_{455}$ tetramer staining. Data show that over time the gDMelapoly plus FAP vaccine group elicited significantly stronger immune responses compared to the gDMelapoly only vaccine group, which were determined by area under the curve followed by Mann-Whitney test.
Figure 3B:
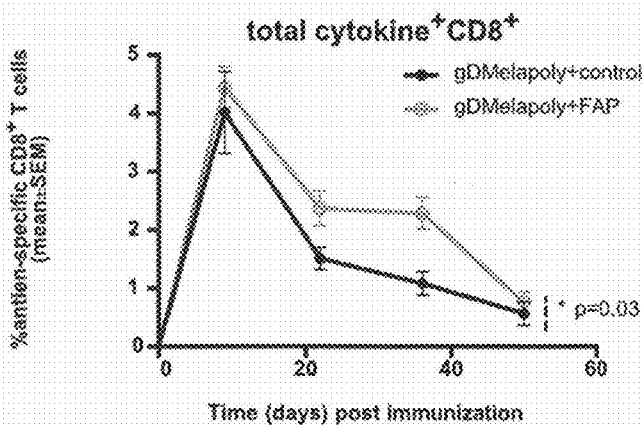
FIG. 3B is a graph measuring the responses of the mice of FIG. 3A was measured by intracellular cytokine staining for production of total cytokines to a combination of eight $CD8^+$ T cell epitopes expressed in the gDMelapoly construct. Data show that over time the gDMelapoly plus FAP vaccine group elicited significantly stronger immune responses compared to the gDMelapoly only vaccine group, which were determined by area under the curve followed by Mann-Whitney test.
Figure 3C:
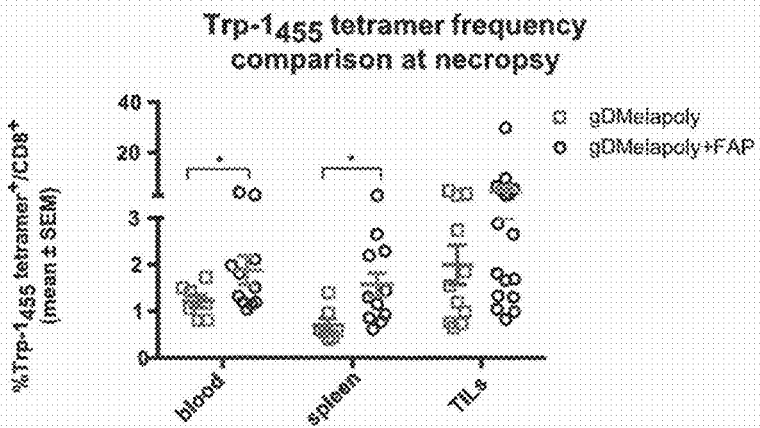
FIG. 3C is a graph demonstrating that at the time of necropsy (when tumors grew to a certain size), significantly higher Trp-$1_{455}$-specific $CD8^+$ T cell frequencies in blood and spleen of mice in the combined vaccination group were detected compared to those from the gDMelapoly only vaccine group. In the tumor the trend of higher Trp-$1_{455}^+$ $CD8^+$ T cell frequencies in the group of mice that received AdC68gD-Melapoly with AdC68mFAP vaccine (p=0.06, one-tailed Mann-Whitney) was also observed.
Figure 8C:
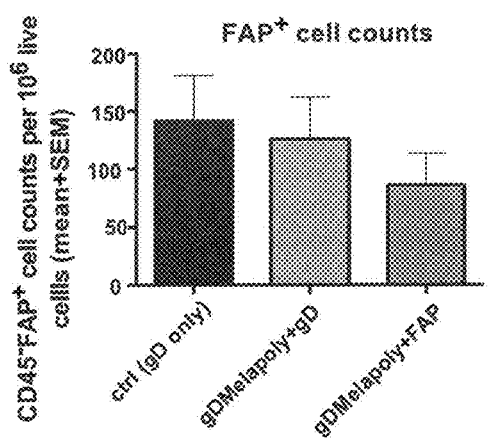
FIG. 8C is a bar graph shows results for a similar vaccination protocol using the control vaccine, the gDMelapoly+control vaccine and the combination of gDMelapoly and the FAP-expressing adenovirus. The combination reduced FAP+ cell counts in the vaccinates. This updated experiment was performed using 5 mice/group, as opposed to the single mouse experiment of FIG. 8A.
Figure 8D:
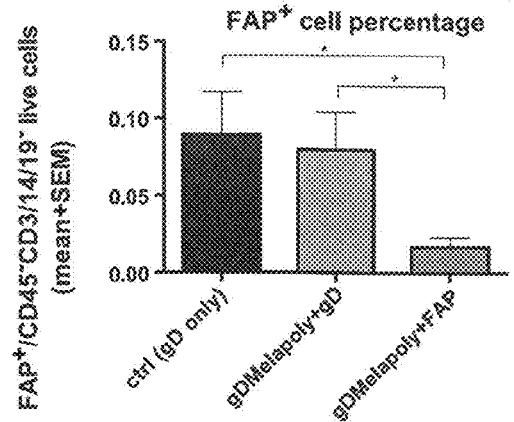
FIG. 8D is a bar graph showing results of FAP+ cell percentage from vaccination according to FIG. 8C protocol. The combination of gDMelapoly and the FAP-expressing adenovirus reduced FAP+ cell percentage in the vaccinates vs. the control and gDMelapoly+control. This experiment was performed using 5 mice/group, as opposed to the single mouse experiment of FIG. 8A.

Inclusion of the AdC68mFAP vector into the vaccination protocol significantly enhanced the magnitude and the cytokine secretion patterns of AdC68gD-Melapoly-induced CD8+ T cells in the peripheral blood and spleen of tumor-bearing mice (FIGS. 2B-2C and 3A-3C). Also detected was a trend of higher Trp-1$_{455}$-specific CD8$^+$ T cell frequencies in the tumor (FIG. 3C). FAP vaccination did reduce numbers of CD3$^-$CD14$^-$CD19$^-$CD45FAP$^+$ cells within the tumors (See FIGS. 8C-8D). Compared to FAP$^-$ cells, FAP$^+$ cells showed enhanced expression of mesenchymal stromal cell markers Sca-1 and CD90.2 (data not shown), which indicated their mesenchymal cell lineage. This cell population may reflect FAP$^+$ fibroblasts that contribute to subversion of the immune responses.

Blood, spleen and TILs from the mice were analyzed upon staining using antibodies to live cells, CD8, CD44, LAG-3-, PD1 and the Trp-1$_{455}$-tetramer. Cells were gated onto live CD8+, CD44$^+$, tet$^+$ cells. FIGS. 9B and 9C show the percentages of Trp-1455-specific CD8$^+$ cells from the three different compartments (blood, spleen and TILs) that highly expressed the indicated co-inhibitory markers. FAP vaccination was shown to reduce expression of immunoinhibitory molecules PD-1 (FIG. 9B) and LAG-3 (FIG. 9C) on MAA-specific CD8+ TIL cells, suggesting better preservation of functions.

Figure 10B:
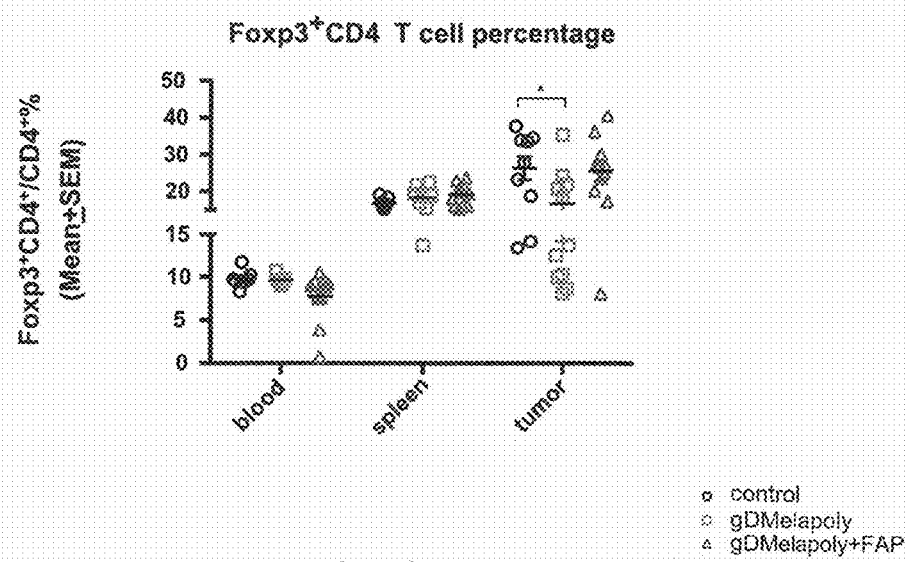
FIG. 10B is an updated graph showing Fox p3+CD4+ T cell percentage in blood, spleen and tumor as between mice vaccinated with control (○), gDMelapoly only (□) or the combination of gD Melapoly with the FAP-expressing adenovirus (Δ).
Figure 10C:
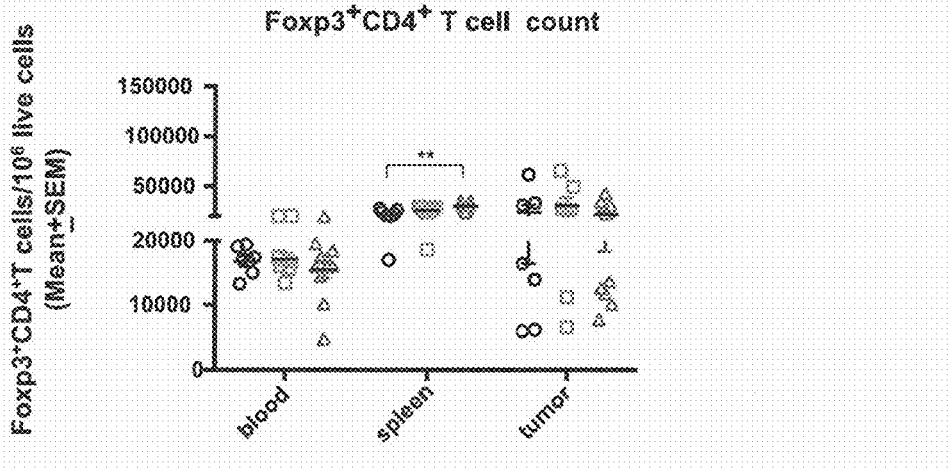
FIG. 10C is an updated graph showing Fox p3+CD4+ T cell count in blood, spleen and tumor as between mice vaccinated with control (○), gDMelapoly only (□) or the combination of gD Melapoly with the FAP-expressing adenovirus (Δ).

Additional preliminary studies were conducted to assess immunoinhibitory cells including regulatory CD4$^+$FoxP3$^+$ T cells and myeloid derived suppressor cells (MDSCs) in vaccinated tumor-bearing mice. MDSCs consist of two subsets: PMN-MDSC, which is CD11b$^+$Gr-1$^{hi}$, and MO-MDSC, which is CD11b$^+$Gr-1$^{int}$ (illustrated in FIG. 11A). MO-MDSC has been shown to be more immunosuppressive[57-58]. Lymphocytes from blood, spleen and tumors of mice vaccinated with AdC68-gD only (control group), AdC68gD-Melapoly combined with AdC68gD, or AdC68gD-Melapoly combined with AdC68mFAP were analyzed upon staining with a live cell stain, and antibodies to cell lineage markers, e.g., CD4 and FoxP3. The graphs of FIGS. 10B-10C and 11C-11F showed both percentages and cell counts of CD4$^+$FoxP3$^+$ cells and the two subsets of MDSCs from different tissues of mice vaccinated with different combinations of vectors at the time of necropsy (when tumors exceeded 1 cm of diameter). Mice vaccinated with AdC68gD-Melapoly showed lower percentages of CD4$^+$FoxP3$^+$ cells in the tumors as compared to mice in the control group (FIG. 10B-10C).

Figure 11E:
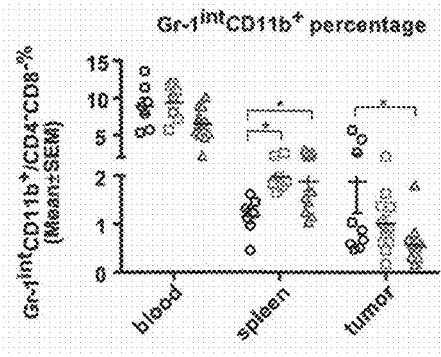
FIG. 11E is a graph showing the percentages of Gr-1$^{int}$CD11b+ cells from blood, spleen and tumors of mice vaccinated as described in FIG. 11C.
Figure 11D:
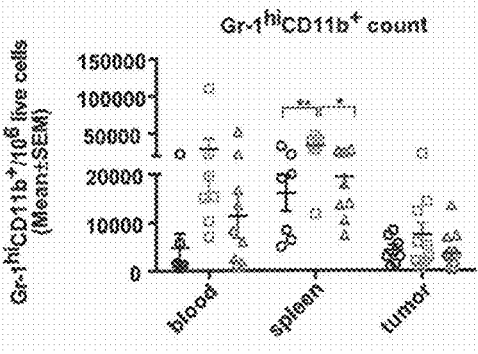
FIG. 11D is a graph from the protocol of FIG. 11C showing the cell count of Gr-1$^{hi}$CD11b+ cells from the indicated tissues.
Figure 11F:
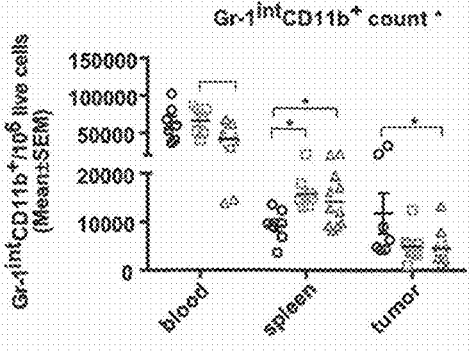
FIG. 11F is a graph from the protocol of FIG. 11E showing the cell count of Gr-1$^{int}$CD11b+ cells from the indicated tissues.

Gr-1$^{hi}$ CD11b$^+$ cells have been reported previously in tumor-bearing mice[37-39]. Their immunosuppressive functions are limited to some tumors and only if cells are present at high numbers. The inventors did not observe much significant changes for this population between different vaccination groups. A modest increase of this subset was found only in the spleen of mice vaccinated with AdC68gD-Melapoly compared to control group mice or mice vaccinated with a combination of AdC68gD-Melapoly and AdC68mFAP, both in terms of percentage over CD4$^-$CD8$^-$ T cells and cell counts per million live cells (FIG. 11 C-11D). On the other hand, the addition of FAP vaccine significantly reduced the percentages and cell counts of Gr-1$^{int}$CD11b$^+$ MO-MDSCs in the tumor compared to those in the tumors of control mice. The same trend was observed in the blood (FIG. 11E-11F). However, an increase of this cell population was seen in the spleens of mice that received the gDMelapoly vaccine (with or without the FAP vaccine) compared to those of control group mice.

Figure 12A:
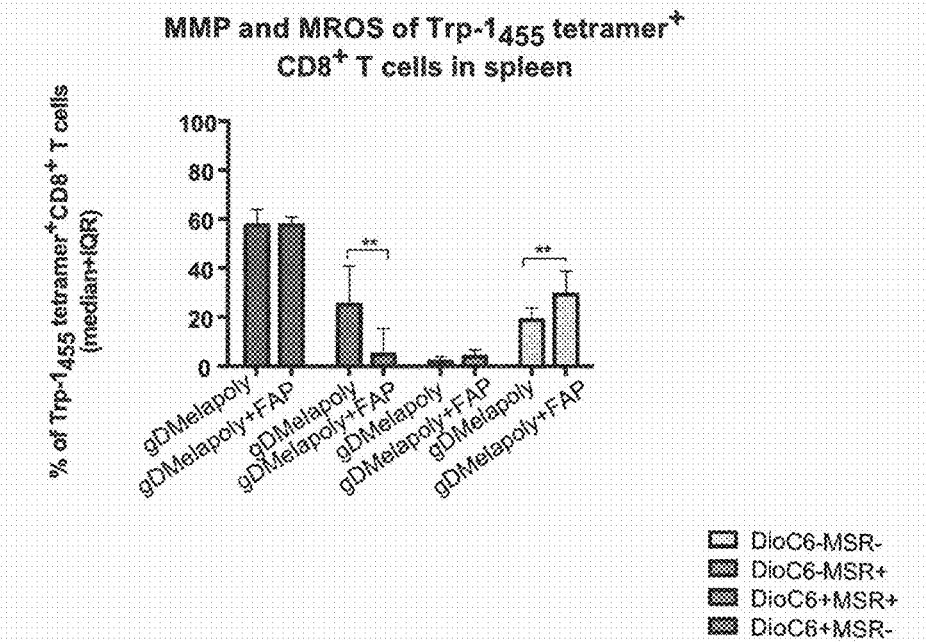
FIG. 12A is a graph showing the analysis of vaccine-induced MAA-specific Trp-1$_{455}$ tetramer+ CD8+ T cells induced with or without AdC68mFAP vaccine in the spleen. Spleen from vaccinated mice were stained with DioC6 which measures mitochondria membrane potential MMP and Mitosox red MSR, a measurement of mitochondria ROS production MROS.
Figure 12B:
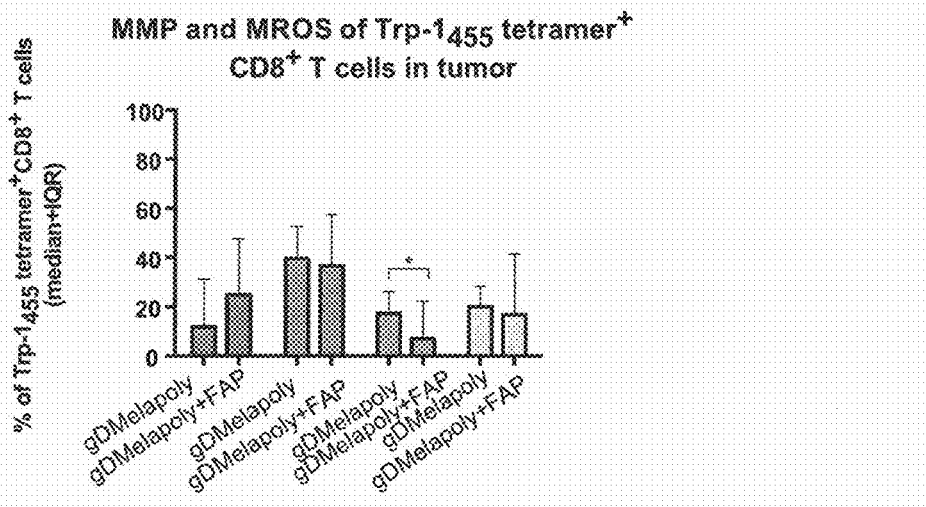
FIG. 12B is a graph showing the analysis of FIG. 12 in tumor tissue from the vaccinated mice.

The metabolic status of vaccine-induced T cells is another important indicator of T cell fitness and could imply the efficacy of cancer vaccines against tumor development. Therefore the metabolism of vaccine-induced MAA-specific CD8+ T cells was analyzed in peripheral tissues and in the tumor. The metabolism of MAA-specific CD8+ T cells induced with AdC68mFAP vaccine was compared with the metabolism of MAA-specific CD8+ T cells induced without AdC68mFAP. The metabolism of T cells was measured by staining spleen and tumor samples of vaccinated mice with DioC6, which measures the mitochondria membrane potential (MMP) and Mitosox red (MSR), which measures the mitochondria ROS production (MROS). Increased MMP or MROS production are signs of cell metabolic stress. As shown in FIG. 12A, in the spleen, the addition of FAP vaccine significantly reduced Trp-1-specific CD8+ T cells that are double positive for DioC6 and Mitosox red and increased the Trp-1-specific CD8+ T cells that are double negative for DioC6 and Mitosox red. This showed that the MAA-specific CD8+ T cells induced in presence of AdC68mFAP were less stressed and likely more resting in the spleen. As shown in FIG. 12B, in the tumor adding FAP vaccine led to significantly reduced percentages of Trp-1-specific CD8+ T cells that are low for MMP and high for MROS production (DioC6$^-$Mitosox red$^+$), further confirming these tumor-filtrating MAA-specific CD8+ T cells were less stressed and could be more potent as compared to those MAA-specific CD8+ TILs induced without FAP vaccine. This reduced metabolic stress is likely achieved by the FAP vaccine's capacity to destroy FAP+ stromal cells, which will lead to increased tumor cell death. As a result this will lift the metabolic stress of tumor-infiltrating MAA-specific CD8+ T cells, which could then exert better tumor-killing function.

The correlation of the metabolic status of MAA-specific CD8+ T cells with their co-inhibitors' expression was further analyzed. As shown in FIG. 13A-13B, in both spleen and tumor the DioC6+ or MSR+ Trp-1$_{455}$-specific CD8+ T cells showed significantly higher PD-1 or LAG-3 expression compared to those that were DioC6$^-$MSR$^-$. This result showed that cells with enhanced metabolic stress by increasing MMP or MROS production are also the ones that showed increased co-inhibitor expression. These cells were more 'exhausted' with reduced cytolytic functions and more prone to apoptosis. The capacity of the AdC68mFAP vaccine to reduce the metabolic stress of MAA-specific CD8+ T cells is shown in FIG. 12A-12B which further explained the improved efficacy of the combined vaccination against tumor development (FIG. 1C).

Example 5: Additional Studies

To determine the immunodominant epitopes of FAP, intracellular cytokine staining (ICS) was performed by incubating PBMC with FAP-expressing fibroblasts to measure the frequency of FAP-specific CD8+ T cells and their ability to secret effective cytokines. Because the efficiency of transfecting FAP-expressing vector to fibroblasts can be low, an IFN-γ ELISPOT assay is performed using peptide pools of murine FAP to define its immunodominant epitopes. ICS was performed by stimulating PBMC only with the dominant peptides.

Antigen-specific CD4+ T cells are usually absent at the tumor site after vaccination, but they are critical for expanding activated CTLs and maintaining an antitumor immune response by providing memory T cells. Therefore to increase presentation of FAP by MHC class II and FAP specific CD4+ T cell responses, the lysosomal targeting signal of mouse LAMP-1 is fused to the C-terminus of mFAP and the signal peptide of mouse heat shock protein gp96 is added to the N-terminus of mFAP[54]. This modified FAP-LAMP directs the endogenously expressed FAP into the lysosome compartments, increasing its presentation by MHC class II and enhancing the magnitude of both FAP-specific CD4+ and CD8+ T cell responses[40,53]. The enhanced frequency of specific CD4+ T cell helps activate FAP-specific B cells and increases their anti-FAP antibody secretion.

HSV gD improves the magnitude but also the quality of the T cell response to the melanoma antigens. Further adding a vaccine/immunogenic composition that targets FAP not only enhances the frequencies of responding CD8+ T cells, but also prevents their functional impairment within the tumor microenvironment.

A summary of the above example is provided below.

1. Early Timepoint Data and Evaluation

All early timepoint data was represented as the mean±standard error. For statistical analyses, a 1-tailed Student's t test was used and P values less than 0.05 are considered significant. Experiments were powered to achieve statistical significance with P values less than 0.05.

As shown in FIG. 1A, all mice injected with melanoma cells (control group) within 25 days developed large tumors, which required euthanasia of the animals. Animals that were injected with tumor cells and then received the AdCgD-Melapoly vaccine/immunogenic composition (+gD only vector to adjust the total virus particles administered for innate immune responses to the vector) showed delayed tumor progression and ~15% of mice survived. Combining the gD-Melapoly vaccine/immunogenic composition with an Ad vector expressing FAP resulted in survival of 45% of animals, a difference that was statistically significant. Mice injected with the vector expressing FAP only showed delayed tumor progression but none of the animals survived (not shown).

The gD-Melapoly vaccine/immunogenic composition, a chimpanzee-origin adenovirus vector that expresses multiple epitopes expressed in melanoma cells linked to herpes simplex virus gD, induced a robust T cell response to these epitopes. The T cell responses of tumor cell injected mice that were immunized with the vaccine/immunogenic composition only were compared to those of mice that also received the FAP vaccine/immunogenic composition by intracellular staining for perforin, granzyme, IFN-γ and TNF-α. Both groups developed T cells with a similar profile to the epitopes expressed by the vaccine/immunogenic composition (data not shown). These data showed that the FAP vector did not increase the T cell response at early timepoints.

To further elucidate the mechanism of improved protection in presence of the FAP expressing vector, mice that had been injected with the FAP expressing vector were tested for CD4+ and CD8+ T cell responses to 16 peptides that reflect likely T cell epitopes of FAP. Both CD4 and CD8 T cell responses could be detected to some of the epitopes (data not shown).

In addition, sera from mice injected with different doses of the FAP expressing vector were tested for antibodies to FAP by an ELISA. As shown in FIG. 4, at the highest dose tested the vector induced a low but detectable antibody response to FAP.

To investigate different T cell populations' contribution to AdC68mFAP vaccine's tumor protection efficacy, mice at the time of tumor injection were depleted for CD4+ or CD8+ T cells or both by treatments with suitable antibodies. Mice were challenged with tumor cells, vaccinated with either control vector expressing gD only or vector expressing FAP on day 3 post tumor challenge. Different groups of mice were treated with depleting antibodies depleting either CD8+/CD4+ T cell population or both from the day of tumor challenge, treated every other day for 3 times. % of survival mice was plotted vs treatment: tumor/no treatment, tumor+ anti-CD8, tumor+anti-CD4, tumor+anti-CD8+anti-CD4, tumor+FAP vaccine, tumor+FAP vaccine+anti-CD8, tumor+ FAP vaccine+anti-CD4. As shown in FIG. 5 depletion of CD8+ T cells abrogated the Ad-FAP (i.e., AdC68m-FAP) vaccine caused or induced delay in tumor progression.

2. Updated Results at Later Timepoints and Further Analysis

For statistical analyses for later timepoint data, Student's t test or ANOVA was used and P values less than 0.05 are considered significant. Experiments were powered to achieve statistical significance with P values less than 0.05.

As shown in FIG. 1B, all mice injected with melanoma cells (control group) within 30 days developed large tumors, which required euthanasia of the animals. Animals that were injected with tumor cells and then received the AdCgD-Melapoly vaccine/immunogenic composition (+gD only vector to adjust the total virus particles administered for innate immune responses to the vector) showed delayed tumor progression and ~15% of mice survived. Combining the gD-Melapoly vaccine/immunogenic composition with an Ad vector expressing FAP resulted in survival of 45% of animals, a difference that was statistically significant. Mice injected with the vector expressing FAP also showed significantly delayed tumor progression compared to control group mice, but none of the animals survived. Moreover, in mice that did developed tumors, the ones that received gDMelapoly and FAP vaccines did so with a significant delay. As illustrated in FIG. 1C, on d25 after tumor challenge, the tumor weights of mice that received the combination vaccines (gDMelapoly+FAP group) were significantly lower compared to those in both the control group and the gDMelapoly+gD vaccination group.

The gD-Melapoly vaccine/immunogenic composition induced a robust T cell response to these epitopes. The T cell responses of tumor cell injected mice that were immunized with the vaccine/immunogenic composition only were compared to those of mice that also received the FAP vaccine/ immunogenic composition by intracellular staining for IFN-γ and TNF-α on days 10 and 35 after vaccination (FIG. 2B-2C). On day 10 both groups developed T cells with a similar profile to the epitopes expressed by the vaccine/ immunogenic composition.

However on day 35, the mice that received a combination of AdC68gD-Melapoly and AdC68mFAP vaccines showed significantly higher percentages of T cells that are IFN-γ$^+$ and TNF-α$^+$ or IFN-γ$^+$ only compared to those of mice that received AdC68gD-Melapoly vaccine alone (FIG. 2C). These data indicated that the addition of FAP vaccine enhances T cell polyfunctionality at later time points after tumor challenge.

The kinetics of MAA-specific CD8$^+$ T cell responses in the blood of mice that received AdC68-gDMelapoly vaccine with or without AdC68mFAP vaccine over time were also compared. These mice were vaccinated 3 days after they were challenged with B16Braf$_{V600E}$ tumor cells. The responses were measured both by Trp-1$_{455}$ tetramer staining and by intracellular cytokine staining for production of total cytokines to a combination of eight CD8$^+$ T cell epitopes expressed in the gDMelapoly construct. As shown in FIG. 3A-3C, over time the gDMelapoly plus FAP vaccine group elicited significantly stronger immune responses compared to the gDMelapoly only vaccine group, which were determined by area under the curve followed by Mann-Whitney test. At the time of necropsy (when tumors grew to a certain size), significantly higher Trp-1$_{455}$-specific CD8$^+$ T cell frequencies in blood and spleen of mice in the combined vaccination group were detected compared to those from the gDMelapoly only vaccine group. In the tumor the trend of higher Trp-1$_{455}^+$ CD8$^+$ T cell frequencies in the group of mice that received AdC68gD-Melapoly with AdC68mFAP vaccine (p=0.06, one-tailed Mann-Whitney) was also observed (FIG. 3C). In conclusion, these data demonstrated that the addition of AdC68mFAP vaccine resulted in significantly enhanced MAA-specific CD8$^+$ T cell responses and improved T cell functions in tumor-challenged mice over time.

To further elucidate the mechanism of improved protection in presence of the FAP expressing vector, both Tyr:: CreER Braf$^{CA/+}$Pten$^{lox/lox}$ transgenic melanoma mice and B16 tumor-challenged C57BL/6 mice were vaccinated with AdC68mFAP vector. CD8$^+$ T cell responses to each of 16 peptides that likely reflect CD8$^+$ T cell epitopes of FAP were measured by ICS. In both tumor models immune response to a majority of the 16 T cell epitopes was detected, and the responses were dominated by cells producing IFN-γ or TNF-α (data not shown)

Each and every patent, patent application, including U.S. patent application Ser. No. 14/212,099, U.S. provisional patent application No. 61/781,429 and publication, including publications listed below, and each and every publically available nucleic acid, amino acid, peptide and vector sequence, cited throughout the disclosure, is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

PUBLICATIONS

1. Uong A, Zon L I., J Cell Physiol 2010; 222(1): 38-41.
2. Algazi A P, Daud A I, Cancer Manag Res 2010; 2: 197-211.
3. Gray-Schopfer V et al, Nature 2007; 445: 851-857.
4. Hodi F S, et al. N Engl J Med 2010; 363:711-723.
5. Trinh V A. Am J Health Syst Pharm 2008; 65:S3-S8.
6. Sivendran S et al. Mt Sinai J Med 2010; 77:620-642.
7. Alexandrescu D, et al. J Immunotherapy 2010; 33:570-590.
8. Stefano I D et al. Biochemical Pharmacology 2009; 78(11): 1374-1381.
9. Schreurs M W et al. Cancer Research 2000; 60: 6995-7001.
10. Bronte V. et al. Cancer Res 2000; 60(2): 253-258.
11. Dankort D, et al. Nature Genetics 2009; 41(5): 544-552.
12. Chin, L. Nat. Rev. Cancer 2003; 3: 559-570.
13. Davies, H. et al. Nature 2002; 417: 949-954.
14. Wellbrock C et al. Cancer Res 2004; 64: 2338-2342.
15. Kaplan J M, et al. J Immunol 1999; 163: 699-707.
16. Weber L W, et al. J. Clin. Invest 1998; 102(6): 1258-1264.
17. Kirwood J M, et al. Clin Cancer Res 2006; 12:2331s-2336s.
18. Overwijk W W et al. J Exp Med 2003; 198(4): 569-580.

19. Guevara-Patino J et al., J. Clin. Invest 2006; 116(5): 1382-1390.
20. Tsukamoto K, et al. EMBO J 1992; 11(2): 519-526.
21. Overwijk W W et al. Proc. Natl. Acad. Sci. 1999; 96: 2982-2987.
22. Naftzger C, et al. Proc. Natl. Acad. Sci. 1996; 93: 14809-14814.
23. Liu Y et al. J Immunol 2009; 182: 5960-5969.
24. Bloom M B. et al, J. Exp. Med. 1997; 185(3): 453-459.
25. Rosenberg S, et al, Nat Med 2004; 10(9): 909-915.
26. Gajewski T F, Clin Cancer Res 2007; 13: 5256-5261.
27. Rosenberg S., Proc. Natl. Acad. Sci. 2008; 105(35): 12643-12644.
28. Bai A, et al., Proc Natl Acad Sci 2008; 105:13003-13008.
29. Singh V. et al, J Immunother 2009; 32(2):129-139.
30. Klebanoff C A et al, Immunological Reviews 2011; 239: 27-44.
31. Murphy K M, et al. Balancing co-stimulation and inhibition with BTLA and HVEM 2006; 6:671-681.
32. Šedý J R et al. Nature Immunology 2005; 6:90-98.
33. Cai G, et al., Immunological Reviews 2009; 229: 244-28.
34. Derré L et al, J. Clin. Invest 2010; 120: 157-167.
35. Lasaro M O et al., Nature Medicine 2008; 14(2): 205-212.
36. DiMenna L, et al. J Immunol 2010; 184(10): 5475-84.
37. Pure E, et al. J. Clin. Invest. 2009; 119: 3613-3625.
38. Bhowmick N, et al. Nature 2004; 432: 332-337.
39. Huber M A., et al. J. Invest. Dermatol. 2003; 120(2): 182-188.
40. Fassnacht M et al. Clin Cancer Res 2005; 11(15): 5566-5571.
41. Wen Y, et al. Cancer Sci 2010; 101(11): 2325-2332.
42. Loeffler M, et al. J. Clin. Invest. 2006; 116(7): 1955-1962.
43. Kraman M, et al, Science 2010; 330(5):827-830.
44. Schreiber H, et al, Science 2010; 330: 761-762.
45. Ariga N, et al., Int. J. Cancer 2001; 95: 67-72.
46. Tatsis N et al, Molecular Therapy 2004; 10(4): 616-629.
47. Tatsis N, et al. Gene Therapy 2006; 13: 421-429.
48. Dankort D, et al. Genes Dev 2007; 21: 379-384.
49. Michaloglou C, et al. Nature 2005; 436: 720-726.
50. Ahmadzadeh M, et al, Blood 2009; 114(8): 1537-1544.
51. Visonneau S, et al. Amer. J. Pathol., 1998; 152(5): 1299-1311.
52. Cheng J D, et al. Cancer Res 2002; 62: 4767-4772.
53. Gilboa E, et al. Cancer Res 2005; 65: 11156-11163.
54. Dannull J, et al. Cancer Res 2002; 62: 5041-5048.
55. Janicki C N, et al, Cancer Res 2008; 68: 2993-3000.
56. Fourcade J et al. J. Exp. Med. 2010; 207(10): 2175-2186.
57. Dolcetti L, et al, Eur J. Immuno. 2010:40:22-35.
58. Priceman S., et al., Blood, 2010; 115:1461-1471.

The invention claimed is:

1. A method for treating cancer or tumor comprising administering to a subject in need thereof an immunogenic composition comprising:
   (a) an adenoviral vector comprising a first expression cassette comprising a first nucleic acid sequence encoding a cancer or tumor-specific antigen fused within or to a protein that inhibits an immunoinhibitory pathway operatively linked to an expression control sequence that directs the expression of the fused antigen in a mammalian host cell; and
   (b) an adenoviral vector comprising a second expression cassette comprising a second nucleic acid sequence encoding a fibroblast activation protein (FAP) operatively linked to an expression control sequence directing the expression of FAP in a mammalian host cell,
   said vectors in a pharmaceutically acceptable carrier suitable for administration to a mammal, and
   wherein the protein that inhibits the pathway is HSV gD, or an antibody or fragment of antibody to PD-1, PD-L1, LAG-1 CTLA-4, BTLA, or CD160.

2. A method for treating a cancer or tumor comprising administering to a subject in need thereof:
   (a) an adenovirus vector comprising a first expression cassette comprising a first nucleic acid sequence encoding a cancer or tumor-specific antigen fused within or to a protein that inhibits an immunoinhibitory pathway operatively linked to an expression control sequence that directs the expression of the fused antigen in a mammalian host cell; and
   (b) an adenovirus vector comprising a second expression cassette comprising a second nucleic acid sequence encoding fibroblast activation protein (FAP) operatively linked to an expression control sequence directing the expression of FAP in a mammalian host cell,
   said vectors in a pharmaceutically acceptable carrier suitable for administration to a mammal, and
   wherein the protein that inhibits the pathway is HSV gD, or an antibody or fragment of antibody to PD-1, PD-L1, LAG-1 CTLA-4, BTLA, or CD160.

3. A method for treating cancer or tumor comprising administering to a subject in need thereof:
   (a) an adenoviral vector comprising a nucleic acid sequence encoding a fusion protein in operative association with an expression control sequence directing the expression of the fusion protein in a mammalian host cell, wherein fusion protein comprises the polyepitope comprising hTrp-2 CD4-88 SEQ ID NO:3, hTrp-2 CD4-237 SEQ ID NO:4, hTrp-2 CD4-449SEQ ID NO:5, hTrp-2 CD8-188 SEQ ID NO:9, hTrp-2 CD8-343 SEQ ID NO:10, hTrp-2 CD8-363 SEQ ID NO:11, mTrp-1 CD8-455 SEQ ID NO:6, mTrp-1 CD8-481 SEQ ID NO:7, mTrp-1 CD8-522 SEQ ID NO:8, human glycoprotein hgp100 CD8-25 SEQ ID NO:12 and Braf-V600E CD8-59 SEQ ID NO:13, the polyepitope fused within HSV-gD; and
   (b) an adenoviral vector comprising a second expression cassette comprising a nucleic acid sequence encoding fibroblast activation protein (FAP) operatively linked to an expression control sequence directing the expression of FAP in a mammalian host cell.

4. The method according to claim 2, wherein vector (a) and vector (b) are the same vector.

5. The method according to claim 2, wherein the tumor-specific antigen of (a) is derived from a cancer that is a melanoma, breast cancer, colon cancer, prostate cancer, cervical cancer, ovarian cancer, or head and neck cancer.

6. The method according to claim 2, wherein the tumor-specific antigen of (a) is a full-length tumor-specific antigen, a mutated tumor-specific antigen, a full-length or mutated tumor-associated antigen, or a polyepitope comprising a fusion of multiple tumor-specific or tumor-associated antigens.

7. The method according to claim 4, wherein the tumor-associated antigen of (a) is one or a multiple of different CD4+ and CD8+ melanoma antigen derived T cell epitopes.

8. The method according to claim 6, wherein the tumor-specific antigen of (a) is a mammalian tyrosinase-related protein 1 (Trp-1) or a mammalian tyrosinase-related protein 2 (Trp-2), or a combination of multiple Trp-1 and Trp-2 epitopes.

9. The method according to claim 2, wherein vector (a) and vector (b) are the same adenovirus vector.

10. The method according to claim 2, wherein vector (a) and vector (b) are independent vectors, each the same or a different adenovirus vector, and wherein the expression control sequences are the same or different for each vector.

11. The method according to claim 2, wherein in vector (b) the second nucleotide sequence encodes FAP fused within or to the protein that inhibits an immunoinhibitory pathway operatively linked to an expression control sequence that directs the expression of the fused antigen in a mammalian host cell, wherein the protein that inhibits the pathway is HSV gD, or an antibody or fragment of antibody to PD-1, PD-L1, LAG-1 CTLA-4, BTLA, or CD160.

12. The method according to claim 2, wherein vector (a) and vector (b) and administered simultaneously or sequentially.

* * * * *

SEQUENCE LISTING

```
<160> NUMBER OF SEQ ID NOS: 13

<210> SEQ ID NO 1
<211> LENGTH: 21
<212> TYPE: PRT
<213> ORGANISM: Plasmodium vivax

<400> SEQUENCE: 1

Gly Met Gln Val Gln Ile Gln Ser Leu Phe Leu Leu Leu Leu Trp Val
1               5                   10                  15

Pro Gly Ser Arg Gly
            20

<210> SEQ ID NO 2
<211> LENGTH: 16
<212> TYPE: PRT
<213> ORGANISM: Artificial Sequence
<220> FEATURE:
<223> OTHER INFORMATION: synthetic T cell epitope

<400> SEQUENCE: 2

Ala Lys Phe Val Ala Ala Trp Thr Leu Lys Ala Ala Ala Ser Glu Gln
1               5                   10                  15

<210> SEQ ID NO 3
<211> LENGTH: 15
<212> TYPE: PRT
<213> ORGANISM: Homo sapiens

<400> SEQUENCE: 3

Arg Lys Phe Phe His Arg Thr Cys Lys Cys Thr Gly Asn Phe Ala
1               5                   10                  15

<210> SEQ ID NO 4
<211> LENGTH: 20
<212> TYPE: PRT
<213> ORGANISM: Homo sapiens
```

<400> SEQUENCE: 4

Asn Glu Ser Phe Ala Leu Pro Tyr Trp Asn Phe Ala Thr Gly Arg Asn
1               5                   10                  15

Glu Cys Asp Val
            20

<210> SEQ ID NO 5
<211> LENGTH: 15
<212> TYPE: PRT
<213> ORGANISM: Homo sapiens

<400> SEQUENCE: 5

Asp Gln Leu Gly Tyr Ser Tyr Ala Ile Asp Leu Pro Val Ser Val
1               5                   10                  15

<210> SEQ ID NO 6
<211> LENGTH: 12
<212> TYPE: PRT
<213> ORGANISM: Mus musculus

<400> SEQUENCE: 6

Thr Ala Pro Asp Asn Leu Gly Tyr Met Ser Glu Gln
1               5                   10

<210> SEQ ID NO 7
<211> LENGTH: 9
<212> TYPE: PRT
<213> ORGANISM: Mus musculus

<400> SEQUENCE: 7

Ile Ala Val Val Asn Ala Leu Leu Leu
1               5

<210> SEQ ID NO 8
<211> LENGTH: 8
<212> TYPE: PRT
<213> ORGANISM: Mus musculus

<400> SEQUENCE: 8

Tyr Ala Tyr Asp Tyr Glu Glu Leu
1               5

<210> SEQ ID NO 9
<211> LENGTH: 9
<212> TYPE: PRT
<213> ORGANISM: homo sapiens

<400> SEQUENCE: 9

Ser Val Tyr Asp Phe Phe Val Trp Leu
1               5

<210> SEQ ID NO 10
<211> LENGTH: 9
<212> TYPE: PRT
<213> ORGANISM: Homo sapiens

<400> SEQUENCE: 10

Ser Thr Phe Ser Phe Arg Asn Ala Leu
1               5

<210> SEQ ID NO 11
<211> LENGTH: 9
<212> TYPE: PRT

```
<213> ORGANISM: Mus musculus

<400> SEQUENCE: 11

Ser Gln Val Met Asn Leu His Asn Leu
1               5

<210> SEQ ID NO 12
<211> LENGTH: 9
<212> TYPE: PRT
<213> ORGANISM: Homo sapiens

<400> SEQUENCE: 12

Lys Val Pro Arg Asn Gln Asp Trp Leu
1               5

<210> SEQ ID NO 13
<211> LENGTH: 9
<212> TYPE: PRT
<213> ORGANISM: mus musculus

<400> SEQUENCE: 13

Phe Gly Leu Ala Asn Glu Lys Ser Ile
1               5
```